US008173819B2

(12) United States Patent  
Rajopadhye et al.

(10) Patent No.: US 8,173,819 B2
(45) Date of Patent: May 8, 2012

(54) NICOTINIC AND PICOLINIC ACID DERIVED NEAR-INFRARED FLUOROPHORES

(75) Inventors: Milind Rajopadhye, Westford, MA (US); Narasimhachari Narayanan, Westford, MA (US); Jeffrey D. Peterson, Shrewsbury, MA (US)

(73) Assignee: VisEn Medical, Inc., Waltham, MA (US)

( * ) Notice: Subject to any disclaimer, the term of this patent is extended or adjusted under 35 U.S.C. 154(b) by 864 days.

(21) Appl. No.: 12/065,391

(22) PCT Filed: Sep. 1, 2006

(86) PCT No.: PCT/US2006/034406
§ 371 (c)(1),
(2), (4) Date: Jun. 13, 2008

(87) PCT Pub. No.: WO2007/028118
PCT Pub. Date: Mar. 8, 2007

(65) Prior Publication Data
US 2008/0267883 A1 Oct. 30, 2008

Related U.S. Application Data

(60) Provisional application No. 60/714,074, filed on Sep. 2, 2005.

(51) Int. Cl.
*C07D 401/06* (2006.01)
(52) U.S. Cl. .................................................. 546/276.7
(58) Field of Classification Search ................ 546/276.7
See application file for complete search history.

(56) References Cited

U.S. PATENT DOCUMENTS

| 3,782,933 | A | * | 1/1974 | Ohlschlager et al. ........... 430/78 |
| 4,264,694 | A | | 4/1981 | Pu et al. |
| 4,370,401 | A | * | 1/1983 | Winslow et al. ............... 430/178 |
| 4,981,977 | A | | 1/1991 | Southwick et al. |
| 5,073,171 | A | | 12/1991 | Eaton |
| 5,268,486 | A | | 12/1993 | Waggoner et al. |
| 5,486,616 | A | | 1/1996 | Waggoner et al. |
| 5,491,151 | A | * | 2/1996 | Nakagawa et al. ........... 514/311 |
| 5,569,587 | A | | 10/1996 | Waggoner |
| 5,569,766 | A | | 10/1996 | Waggoner et al. |
| 5,593,658 | A | | 1/1997 | Bogdanov et al. |
| 5,605,809 | A | | 2/1997 | Komoriya et al. |
| 5,627,027 | A | | 5/1997 | Waggoner |
| 5,808,044 | A | | 9/1998 | Brush et al. |
| 5,877,310 | A | | 3/1999 | Reddington et al. |
| 6,002,003 | A | | 12/1999 | Shen et al. |
| 6,004,536 | A | | 12/1999 | Leung et al. |
| 6,008,373 | A | | 12/1999 | Waggoner et al. |
| 6,027,709 | A | | 2/2000 | Little et al. |
| 6,043,025 | A | | 3/2000 | Minden et al. |
| 6,083,485 | A | | 7/2000 | Licha et al. |
| 6,083,486 | A | | 7/2000 | Weissleder et al. |
| 6,127,134 | A | | 10/2000 | Minden et al. |
| 6,130,094 | A | | 10/2000 | Waggoner et al. |
| 6,133,445 | A | | 10/2000 | Waggoner et al. |
| 6,136,612 | A | | 10/2000 | Della Ciana et al. |
| 6,248,904 | B1 | | 6/2001 | Zhang et al. |
| 6,258,340 | B1 | | 7/2001 | Licha et al. |
| 6,448,008 | B1 | | 9/2002 | Caputo et al. |
| 6,534,041 | B1 | | 3/2003 | Licha et al. |
| 6,592,847 | B1 | | 7/2003 | Weissleder et al. |
| 6,740,755 | B2 | | 5/2004 | Caputo et al. |
| 6,747,159 | B2 | | 6/2004 | Caputo et al. |
| 6,869,593 | B2 | | 3/2005 | Frangioni |
| 6,913,743 | B2 | | 7/2005 | Licha et al. |
| 6,926,885 | B2 | | 8/2005 | Licha et al. |
| 7,025,949 | B2 | | 4/2006 | Licha et al. |
| 7,374,746 | B2 | | 5/2008 | Frangioni |
| 7,445,767 | B2 | | 11/2008 | Licha et al. |
| 7,647,091 | B2 | | 1/2010 | Ntziachristos et al. |
| 7,655,217 | B2 | | 2/2010 | Licha et al. |
| 7,947,256 | B2 | | 5/2011 | Rajopadhye et al. |
| 2003/0044353 | A1 | | 3/2003 | Weissleder et al. |
| 2005/0169843 | A1 | | 8/2005 | Weissleder et al. |
| 2006/0099712 | A1 | | 5/2006 | Gilman et al. |
| 2006/0275775 | A1 | | 12/2006 | Weissleder et al. |
| 2008/0102036 | A1 | | 5/2008 | Poss et al. |
| 2008/0226562 | A1 | | 9/2008 | Groves et al. |
| 2008/0267883 | A1 | | 10/2008 | Rajopadhye et al. |
| 2008/0286207 | A1 | | 11/2008 | Narayanan |
| 2008/0312540 | A1 | | 12/2008 | Ntziachristos |
| 2008/0317676 | A1 | | 12/2008 | Rajopadhye et al. |

(Continued)

FOREIGN PATENT DOCUMENTS

EP 0417941 3/1991

(Continued)

OTHER PUBLICATIONS

Becker et al. (2000) "Macromolecular Contrast Agents for Optical Imaging of Tumors: Comparison of Indotricarbocyanine-labeled Human Serum Albumin and Transferrin," *Photochem. Photobiol.* 72:234-241.
Brasseur et al. (1999) "Receptor-Mediated Targeting of Phthalocyanines to Macrophages via Covalent Coupling to Native or Maleylated Bovine Serum Albumin," *Photochem. Photobiol.* 69:345-352.
Gatter et al. (1983) "Transferrin Receptors in Human Tissues: Their Distribution and Possible Clinincal Relevance," *J. Clin. Pathol.* 36:539-545.
Hamblin et al. (1994) "Photosensitizer Targeting in Photodynamic Therapy. I. Conjugates of Haematoporphyrin with Albumin and Transferrin," *J. Photochem. Photobiol. B.* 26(1):45-56.

(Continued)

*Primary Examiner* — Robert Havlin
(74) *Attorney, Agent, or Firm* — Goodwin Procter LLP

(57) ABSTRACT

This invention relates to new fluorescent chemical entities, including fluorescent molecules that comprise a carboxyl or carbonyl functionalized pyridine moiety. This invention also relates to the corresponding reactive versions of such molecules. This invention also relates to the corresponding conjugates with moieties such as peptides, proteins, various biomolecules, carbocyclic and heterocyclic compounds, sugars, and their uses thereof.

20 Claims, 1 Drawing Sheet

U.S. PATENT DOCUMENTS

| | | | |
|---|---|---|---|
| 2009/0068115 A1 | 3/2009 | Gaw et al. |
| 2009/0123383 A1 | 5/2009 | Frangioni |
| 2009/0130024 A1 | 5/2009 | Narayanan et al. |
| 2009/0220430 A1 | 9/2009 | Rajopadhye et al. |
| 2010/0074847 A1 | 3/2010 | Madden et al. |
| 2010/0078576 A1 | 4/2010 | Ntziachristos et al. |
| 2010/0129293 A1 | 5/2010 | Licha et al. |
| 2010/0166659 A1 | 7/2010 | Licha et al. |
| 2010/0172841 A1 | 7/2010 | Peterson et al. |
| 2010/0189657 A1 | 7/2010 | Weissleder et al. |
| 2010/0268070 A1 | 10/2010 | Jaffer et al. |
| 2011/0152501 A1 | 6/2011 | Weissleder et al. |
| 2011/0165075 A1 | 7/2011 | Rajopadhye et al. |
| 2011/0171136 A1 | 7/2011 | Poss et al. |

FOREIGN PATENT DOCUMENTS

| | | |
|---|---|---|
| EP | 0820057 | 1/1998 |
| EP | 1065250 | 1/2001 |
| EP | 1090961 | 4/2001 |
| EP | 1219626 | 7/2002 |
| JP | 10071766 | 3/1998 |
| WO | WO-97/40104 | 10/1997 |
| WO | WO-99/31181 | 6/1999 |
| WO | WO-99/51702 | 10/1999 |
| WO | WO-00/16810 | 3/2000 |
| WO | WO-01/21624 | 3/2001 |
| WO | WO-2007/028163 | 3/2007 |
| WO | WO-2009/114776 | 9/2009 |

OTHER PUBLICATIONS

Hansch et al. (2004) "Diagnosis of Arthritis Using Near-Infrared Fluorochrome Cy5.5," *Investigative Radiology* 39(10):626-632.

Kremer et al. (2000) "Laser-Induced Fluorescence Detection of Malignant Gliomas Using Fluorescein-Labeled Serum Albumin: Experimental and Preliminary Clinical Results," *Neurol. Res.* 22(5):481-489.

Montet et al. (2006) "An Albumin-Activated Far-Red Fluorochrome for In Vivo Imaging," *ChemMedChem.* 1(1):66-69.

Parmelee et al. (1997) "Preclinical Evaluation of the Pharmokinetics, Biodistribution and Elimination of MS-325, a Blood Pool Agent for Magnetic Imaging Resonance," *Investigative Radiology* 32(12):741-747.

Rennen et al. (2001) "The Effect of Molecular Weight on Nonspeciific Accumulation of (99m) T-Labeled Proteins in Inflammatory Foci," *Nucl. Med. Biol.* 28(4):401-408.

Schilling et al. (1992) "Design of Compounds Having Enhanced Tumour Uptake, Using Serum Albumin as a Carrier—Part II. In Vivo Studies," *Int. J. Rad. Appl. Instrum. B* 19(6):685-695.

Tromberg et al. (1997) "Non-Invasive Measurements of Breast Tissue Optical Properties Using Frequency-Domain Photo Migration," *Phil. Trans. R. Soc. Lond. B* 352:661-668.

Wang et al. (2001) "Amplified Delivery of Indium-111 to EGFR-Positive Human Breast Cancer Cells," *Nucl. Med. Biol.* 28:895-902.

Williams et al. (1993) "Comparison of Covalent and Noncovalent Labeling with Near-Infrared Dyes for the High-Performance Liquid Chromatographic Determination of Human Serum Albumin," *Anal. Chem.* 65:601-605.

Wyatt (1997) "Cerebral Oxygenation and Haemodynamics in the Fetus and Newborn Infant," *Phil. Trans. R. Soc. Lond. B* 352:697-700.

Ciernik et al. (1972) "New Synthesis of Neocyanine Dyes Containing Three Heterocycles," *Collection of Czechoslovak Chemical Communications* 37(11):3800-3807. Abstract only.

Ciernik et al. (1972) "New Pentamethinecyanine Dyes," *Collection of Czechoslovak Chemical Communications* 37(8):2771-2778. Abstract only.

International Search Report and Written Opinion for International Patent Application No. PCT/US2006/034604, dated Jan. 31, 2007, 11 pages.

Bredereck et al. (1970) "Syntheses in the Heterocyclic Series. XIV. Formylation of 4-methylpyrimidine and Reactions of 2-(4-pyrimidinyl)malonaldehyde," *Justus Liebigs Annalen der Chemie* 737:46-52. Abstract only.

Ernst et al. (1989) "Cyanine Dye Labelling Reagents for Sulphydryl Groups," *Cytometry* 10:3-10.

Ficken, (1971) "The Chemistry of Synthetic Dyes," vol. 4, K. Venkataraman Ed., Academic Press, New York, p. 210-223.

Fry (1977) "Cyanine Dyes and Related Compounds," *Rodd's Chemistry of Carbon Compounds* Elsevier, Amsterdam. vol. IVb, Chapter 15, p. 369-424.

International Search Report and Written Opinion for International Patent Application No. PCT/US2006/034260, dated Jan. 31, 2007, 9 pages.

Lindsey et al. (1989) "Visible Light Harvesting in Covalently-Linked Porphyrin Cyanine Dyes," *Tetrahedron* 45:4845-4866.

Mujumdar et al. (1989) "Cyanine Dye Labelling Reagents Containing Isothiocyanate Groups," *Cytometry* 10:11-19.

Mujumdar et al. (1993) "Cyanine Dye Labelling Reagents: Sulfoindocyanine Succinimidyl Esters," *Bioconjugate Chemistry* 4:105-111.

Mujumdar et al. (1996) "Cyanine Labelling Reagents: Sulfobenzoindocyanine Succinimidyl Esters," *Bioconjugate Chemistry* 7:356-362.

Ozmen et al. (2000) "Infrared Fluorescence Sensing of Submicromolar Calcium: Pushing the Limits of Photoinduced Electron Transfer," *Tetrahedron Letters* 41:9185-9188.

Sun et al. (2006) "'Clickable' Nanoparticles for Targeted Imaging," *Molecular Imaging* 5(2):122-128.

International Search Report of the International Searching Authority for PCT/US2006/034406 dated Feb. 15, 2007, 5 pages.

Written Opinion of the International Searching Authority for PCT/US2006/034406 dated Feb. 15, 2007, 6 pages.

Dorwald F.A. (2005) Side Reactions in Organic Synthesis, Wiley: VCH, Weinheim, pp. preface and 1-16.

Adams et al. (1989) "Di(1-pyridinio)- und Di(1-bipyridindiio)-dihydrodibenzo[14]annulene," *Angewandte Chemie* 101(8):1043-1046.

\* cited by examiner

NICOTINIC AND PICOLINIC ACID DERIVED NEAR-INFRARED FLUOROPHORES

RELATED APPLICATION

This application claims the benefit of U.S. Provisional Application No. 60/714,074, filed on Sep. 2, 2005.

The entire teachings of the above application are incorporated herein by reference.

BACKGROUND OF THE INVENTION

Optical imaging is an evolving clinical imaging modality that uses penetrating light rays to create images. Light in the red and near-infrared (NIR) range (600-1200 nm) is used to maximize tissue penetration and minimize absorption from natural biological absorbers such as hemoglobin and water. (Wyatt, *Phil. Trans. R. Soc. London B* 352:701-706, 1997; Tromberg, et al., *Phil. Trans. R. Soc. London B* 352:661-667, 1997).

Besides being non-invasive, optical imaging methods offer a number of advantages over other imaging methods: they provide generally high sensitivity, do not require exposure of test subjects or lab personnel to ionizing radiation, can allow for simultaneous use of multiple, distinguishable probes (important in molecular imaging), and offer high temporal and spatial resolution (important in functional imaging and in vivo microscopy, respectively).

In fluorescence imaging, filtered light or a laser with a defined bandwidth is used as a source of excitation light. The excitation light travels through body tissues. When it encounters a reporter molecule (i.e., contrast agent or imaging has detectably different properties from the excitation light. The resulting emitted light then can be used to construct an image.

Most optical imaging techniques have relied on the use of organic and inorganic fluorescent molecules as the reporter molecule.

Fluorescent dyes are generally known and used for fluorescence labeling and detection of various biological and non-biological materials by procedures such as fluorescence microscopy, fluorescence immunoassay and flow cytometry. A typical method for labeling such materials with fluorescent dyes is to create a fluorescent complex by means of bonding between suitable groups on the dye molecule and compatible groups on the material to be labeled. In this way, materials such as cells, tissues, amino acids, proteins, antibodies, drugs, hormones, nucleotides, nucleic acids, lipids and polysaccharides and the like may be chemically labeled and detected or quantified, or may be used as fluorescent probes which can bind specifically to target materials and detected by fluorescence detection methods. Brightly fluorescent dyes permit detection or location of the attached materials with great sensitivity.

Certain carbocyanine or polymethine dyes have demonstrated utility as labeling reagents for a variety of biological applications, e.g. U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); also WO 97/40104, WO 99/51702, WO 01/21624, and EP 1 065 250 A1; and Tetrahedron Letters 41, 9185-88 (2000); all of the above incorporated by reference.

Comprehensive reviews regarding polymethine dyes have been by written by L. G. S. Brooker, "The Theory of the Photographic Process" Mees Ed., Macmillan, New York, (1942), p. 987 and (1966), p. 198; Frances M. Hamer, in "The Chemistry of Heterocyclic Compounds", Vol 18, "The Cyanine Dyes and Related Compounds", Weissberger, Ed, Wiley Interscience, New York, (1964); G. E. Ficken, "The Chemistry of Synthetic Dyes", Vol 4, K. Venkataraman Ed., Academic Press, New York, (1971), p. 211; A. I. Kiprianov, Usp. Khim., 29, 1336, (1960), 35, 361 (1966), 40, 594 (1971); D. W. Heseltine, "The Theory of the Photographic Process", 4.sup.th edition, James Ed., Macmillan, New York, (1977), chapter 8, "Sensitising and Desensitising Dyes"; S. Daehne, Phot. Sci. Eng., 12, 219 (1979); D. J. Fry, "Rodd's Chemistry of Carbon Compounds", "Cyanine Dyes and Related Compounds", Vol. IVb, chapter 15, p. 369 Elsevier, Amsterdam, (1977); Supplement to Vol. IVb, 2.sup.nd Edition (1985), p. 267; H. Zollinger, "Color Chemistry", VCH, Weinheim (1987), chapters 3 and 14; D. M. Sturmer, "The Chemistry of Heterocyclic Compounds", "Special Topics in Heterocyclic Chemistry", chapter VIII, "Synthesis and Properties of Cyanine and Related Dyes", Weissberger Ed., Wiley, New York, (1977); "The Kirk-Othmer Encyclopaedia of Chemical Technology" Vol 7, p. 782, "Cyanine Dyes", Wiley, New-York, (1993).

To be useful as a label, a dye has to be provided with a suitable side chain containing a functional group. The method and site of introduction of a side chain containing a functional group into the structure for the purpose of conjugation, or binding to another molecule, represents the innovative step in the inventions concerning the use of the dye as a labeling reagent. Typically, only one such functionalized side arm is used in order to avoid cross-linking or purification problems. One aspect in the design of polymethine labeling reagents has been to attach the functionalized side arm to one of the heterocyclic nuclei of the dye, formula (1):

$$Z^1\text{-PML-}Z^2 \quad (1)$$

See, for instance: J. S. Lindsey, P. A. Brown, and D. A. Siesel, "Visible Light-Harvesting in Covalently-Linked Porphyrin-Cyanine Dyes, Tetrahedron, 45, 4845, (1989); R. B. Mujumdar, L. A. Ernst, S. R. Mujumdar, and A. S. Waggoner, "Cyanine Dye Labelling Reagents Containing Isothiocyanate Groups", Cytometry, 10, 11 (1989); L. A. Ernst, R. K. Gupta, R. B. Mujumdar, and A. S. Waggoner, "Cyanine Dye Labelling Reagents for sulphydryl Groups", Cytometry, 10, 3, (1989); P. L. Southwick P. L., L. A. Ernst, E. W. Tauriello, S. R. Parker, R. B. Mujumdar, S. R. Mujumndar, H. A. Clever, and A. S. Waggoner, "Cyanine Dye Labelling Reagents-Carboxymethylindocyanine Succinimidyl Esters", Cytometry 11, 418 (1990); R. B. Mujumdar, L. A. Ernst, Swati R. Mujumdar, C. J. Lewis, and A. S. Waggoner, "Cyanine Dye Labelling Reagents: Sulfoindocyanine Succinimidyl Esters", Bioconjugate Chemistiy, 4, 105, (1993); A. J. G. Mank, E. J. Molenaar, H. Lingeman, C. Goojer, U. A. Th. Brinkman, and N. H. Velthorst, "Visible Diode Laser Induced Fluorescence Detection in Liquid Chromatography after Precolumn Derivatisation of Thiols", Anal. Chem., 65, 2197, (1993); H. Yu., J. Chao, D. Patek, S. R. Mujumdar, and A. S. Waggoner, "Cyanine dye dUTP analogs for enzymatic labelling of DNA Probes", Nucl. Acids Res 22, 3226, (1994); Z. Zho, J. Chao, H. Yu, and A. S. Waggoner, "Directly labelled DNA probes using fluorescent nucleotides with different length linkers", Nucl. Acids, Res, 22, 3226. A. J. G. Mank, H. T. C. van der Laan, H. Lingeman, Cees Goojer, U. A. Th. Brinkman, and N. H. Velthorst, "Visible Diode Laser-Induced Fluorescence Detection in Liquid Chromatography after Precolumn Derivatisation of Amines", Anal. Chem., 67, 1742, (1995); S. R. Mujumdar, R. B. Mujumdar, C. M. Grant, and A. S. Waggoner, "Cyanine Labelling Reagents: sulfobenzoindocyanine succinimidyl esters", Bioconjugate Chemistry, 7, 356, (1996). Patent Literature: P. L. Southwick, and A. S. Waggoner, "Intermediate for and Fluorescent Cyanine Dyes containing Carboxylic Acid Groups", U.S. Pat. No. 4,981,977, Jan. 1, 1991; A. S. Waggoner, L. A. Ernst, and Mujumdar, R. B., "Method for Labelling and Detecting Materials Employing Arylsulfonate Cyanine Dyes", U.S. Pat. No. 5,268,486, Dec. 7., 1993; A. S. Waggoner, "Cyanine Dyes as Labelling Reagents for Detection of Biological and Other Materials by Luminescence Methods", U.S. Pat. No. 5,627,027, May 6, 1996; A. S. Waggoner, and R. B. Mujumdar, "Rigidised Trimethine Cyanine Dyes", WO99/311181; G.-Y. Shen, T. S. Dobashi, "Cyanine Dye Activating Group with Improved Coupling Selectivity"; T. S. G. M. Little, R. Raghavachari; N. Narayanan; H. L. Osterman, "Fluorescent Cyanine Dyes", U.S. Pat. No. 6,027,709, Feb. 22, 2000.

The general synthetic strategy necessary to prepare these labeling reagents is as follows. First, a quaternized nitrogen heterocycle $Z^1$ is prepared. Then, this heterocyclic base is reacted with a polymethine linker (PML) that is an electrophilic reagent such as PhNH—(CH=CH)$_n$—CH=NHPh.HCl or RO—(CH=CH)$_n$—CH(OR)$_2$, P where Ph is a phenyl ring and R a methyl or ethyl group, to obtain a so-called hemicyanine dye, $Z^1$—(CH=CH)$_n$ NHPh or $Z^1$—(CH=CH)$_n$ NAcPh, where Ac is the acetyl radical, or $Z^1$—(CH=CH)$_n$—OR. These intermediates are then reacted with a different quaternary nitrogen heterocycle, $Z^2$. The functionalized side arm can be attached either to the first or to the second quaternized nitrogen heterocycle.

The hemicyanine intermediates, however, can be difficult to obtain in good yields and/or in a pure form (see, for example, F. M. Hamer, "Some Unsymmetrical Pentamethincyanine Dyes and their Tetramethin Intermediates", J. Chem. Soc., 32 (1949) and R. B. Mujumdar, L. A. Ernst, Swati R. Mujumdar, C. J. Lewis, and A. S. Waggoner, "Cyanine Dye Labelling Reagents: Sulfoindocyanine Succinimidyl Esters", Bioconjugate Chemistry, 4, 105, (1993).

Thus polymethine dyes that are efficient and easy to produce as well as suitable for preparing conjugates with biomolecules are desirable.

SUMMARY OF THE INVENTION

Fluorescent dye compounds with a polymethine linker bridge that are bright, highly fluorescent dyes that absorb and emit between about 440 and about 1100 nm, have now been discovered.

The present invention is directed to fluorescent dye compounds with a polymethine linker bridge that has been modified by a carboxyl containing pyridine ring which are capable of producing strong fluorescence in the 600 nm to 900 m region of the spectrum and also contain functional groups and/or solubilizing groups which render the dye suitable for covalent labeling, in particular to biological molecules and other target materials.

In one embodiment, the present invention is directed to a polymethine fluorochrome compound represented by formulae (2) or a salt thereof:

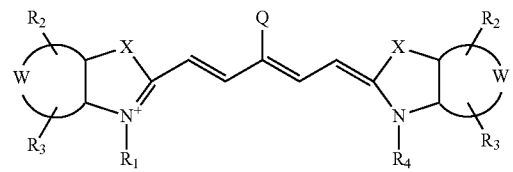

(2)

X is independently selected from the group consisting of C(CH$_2$Y$_1$)(CH$_2$Y$_2$), O, S, and Se;

Y$_1$ and Y$_2$ are independently selected from the group consisting of H, C$_1$-C$_{20}$ aliphatic group and a C$_1$-C$_{20}$ aliphatic group substituted with —OR*, N(R*)$_2$ or —SR*;

W represents a benzo-condensed, a naphtho-condensed or a pyrido-condensed ring;

R$_1$ is selected from the group consisting of H, (CH$_2$)$_x$CH$_3$, (CH$_2$)$_n$SO$_3^-$ and (CH$_2$)$_n$SO$_3$H, wherein x is an integer selected from 0 to 6 and n is an integer selected from 2 to 6;

R$_4$ is selected from the group consisting of H, (CH$_2$)$_x$CH$_3$, (CH$_2$)$_n$SO$_3^-$ and (CH$_2$)$_n$SO$_3$H, wherein x is an integer selected from 0 to 6 and n is an integer selected from 2 to 6;

R$_2$ and R$_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a heteroaryl ring substituted with a carboxyl group or 6-membered heteroaryl ring substituted with a carbonyl group.

In another embodiment present invention is directed to a polymethine fluoro chrome compound represented by formulae (2) or a salt thereof when:

X is independently selected from the group consisting of C(CH$_2$Y$_1$)(CH$_2$Y$_2$), O, S, and Se;

Y$_1$ and Y$_2$ are independently selected from the group consisting of H, C$_1$-C$_{20}$ aliphatic group and a C$_1$-C$_{20}$ aliphatic group substituted with —OR*, N(R*)$_2$ or —SR*;

W represents a benzo-condensed, a naphtho-condensed or a pyrido-condensed ring;

R$_1$ is selected from the group consisting of (CH$_2$)$_x$CH$_3$, (CH$_2$)$_n$SO$_3^-$ and (CH$_2$)$_n$SO$_3$H, wherein x is an integer selected from 0 to 6 and n is an integer selected from 2 to 6;

R$_4$ is selected from the group consisting of (CH$_2$)$_x$CH$_3$, (CH$_2$)$_n$SO$_3^-$ and (CH$_2$)$_n$SO$_3$H, wherein x is an integer selected from 0 to 6 and n is an integer selected from 2 to 6;

R$_2$ and R$_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a heteroaryl ring substituted with a carboxyl group or 6-membered heteroaryl ring substituted with a carbonyl group.

In another embodiment, the present invention is directed to a biocompatible fluorescent molecule comprising one or more biomolecules chemically linked to a compound of the present invention.

In another embodiment, the present invention is directed to a biocompatible fluorescent molecule comprising a biomolecule chemically linked to a compound of the present invention, wherein the compound has an absorption and emission maxima between about 500 nm and about 900 nm.

In another embodiment, the present invention is directed to a biocompatible fluorescent molecule comprising a biomolecule chemically linked to a compound of the present invention wherein the biocompatible fluorescent molecule is activated after target interaction.

In another embodiment, the present invention is directed to a biocompatible fluorescent molecule comprising a biomolecule chemically linked to a compound of the present invention wherein the biocompatible fluorescent molecule has a high binding affinity to a target.

In another embodiment, the present invention is directed to a method of in vivo optical imaging, the method comprising:
(a) administering to a subject a compound or biocompatible fluorescent molecule of the present invention
(b) allowing time for the compound or biocompatible fluorescent molecule to distribute within the subject or to contact or interact with a biological target;
(c) illuminating the subject with light of a wavelength absorbable by the compound or biocompatible fluorescent molecule; and
(d) detecting the optical signal emitted by the compound or biocompatible fluorescent molecule.

In another embodiment, the present invention is directed to a biocompatible fluorescent molecule comprising a biomolecule chemically linked to a compound of the present invention, wherein the biocompatible fluorescent molecule is a labeled cell.

DETAILED DESCRIPTION OF THE INVENTION

Figure 1:
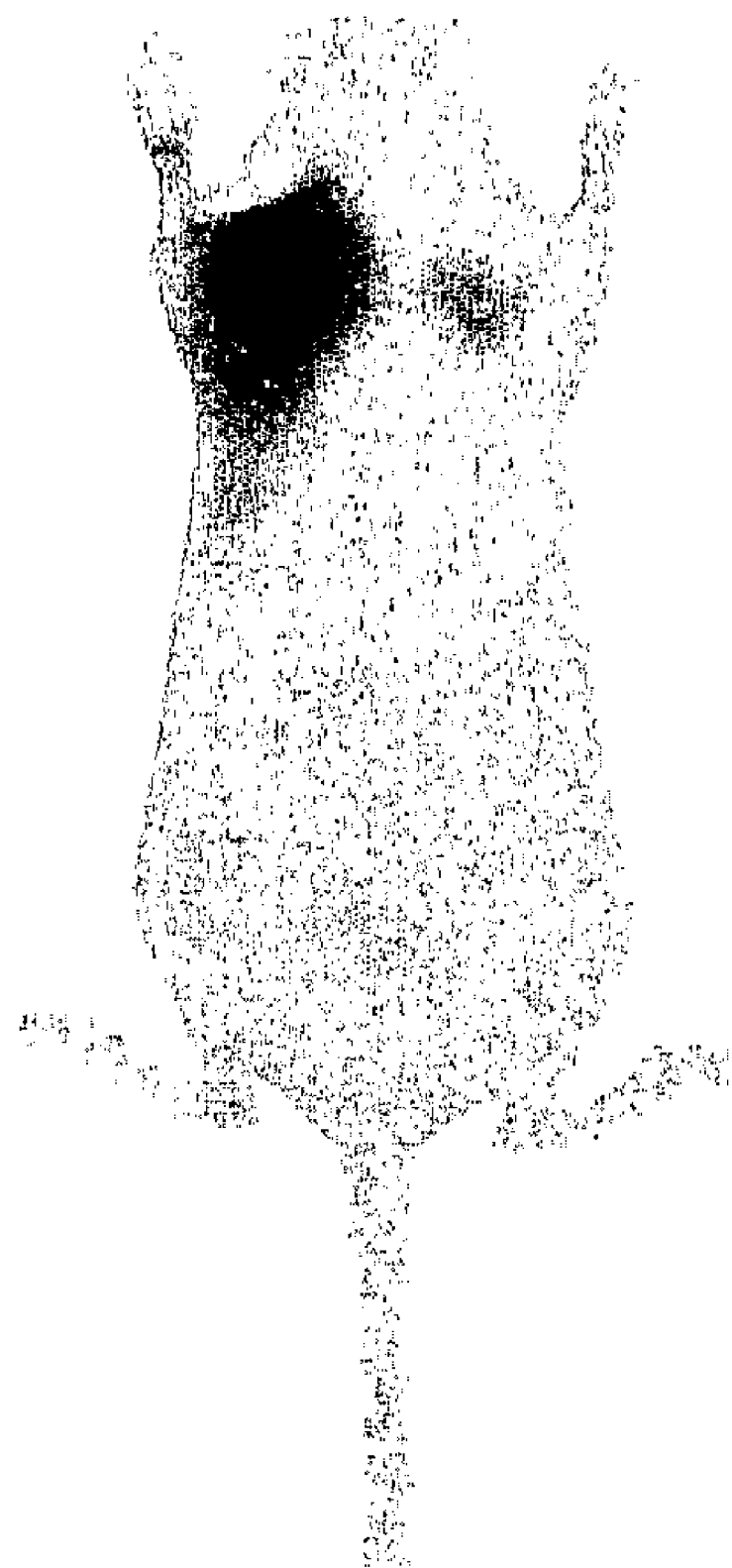
FIG. 1 is a fluorescence image of a compound of the present invention in tumors of a female NU/NU mice (6-8 weeks old) after 24 hrs on a fluorescence reflectance system (FRI, Kodak 2000 MM) system.

A description of preferred embodiments of the invention follows.

The present invention is directed to bright, highly fluorescent compounds (dyes) that absorb and/or emit between about 440 and about 1100 nm, between about 550 and about 800 nm, between about 500 and about 900 nm or between about 600 and about 900 nm and conjugates thereof. It will be appreciated that compounds (fluorochromes) with excitation and emission wavelengths in other spectrums, such as the visible and ultraviolet light spectrum, are also encompassed by the present invention.

The structures of the compounds of the present invention, in general are based on nicotinic acid and picolinic acid derivatives that confer high quantum yields of fluorescence. Moreover, in certain embodiments of the present invention the compounds contain functional or reactive groups which may be used to chemically link with complementary groups on target molecules.

"Chemically linked" or "chemically link" means connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions. This also includes crosslinking or caging.

The term "compounds," as used herein, refers to "polymethine fluorochromes", "fluoroclromes", "fluorescent dyes", "cyanine dyes" "carbocyanine dyes" and "dyes" of the instant invention. These terms are used interchangeably to refer to the compounds of the instant invention.

In one embodiment, the compounds of the invention comprise two heterocyclic ring systems bound together by a polymethine linker (PML), according to the formula (1):

$$Z^1\text{-(PML)-}Z^2 \tag{1}$$

wherein $Z^1$ is a heterocyclic ring system such as an indolinium ring, $Z^2$ is a second heterocyclic ring system, such as, an indolinium ring, and PML is a polymethine linker that is substituted with a carboxyl containing heterocyclic ring, such as, pyridine. The $Z^1$ and $Z^2$ ring systems are optionally further substituted by a variety of substituents or are fused to additional rings that are optionally further substituted.

In one aspect, the compounds of the present invention are further substituted one or more times by sulfo or sulfoalkyl. By "sulfo" is meant sulfonic acid, or salt of sulfonic acid (sulfonate). Similarly, by "carboxyl" is meant carboxylic acid, carboxylate ester or salt of carboxylic acid. "Phosphate" is an ester of phosphoric acid, and includes salts of phosphate. "Phosphonate" means phosphonic acid and includes salts of phosphonate. Similarly for "carbonyl" groups such as, but not limited to carbonyl halode, (e.g., chloride) and carboxamide are included. As used herein, unless otherwise specified, the alkyl portions of substituents such as alkyl, alkoxy, arylalkyl, alkylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

In one embodiment the present invention is directed to a compound represented by formulae (2) or a salt thereof, wherein:

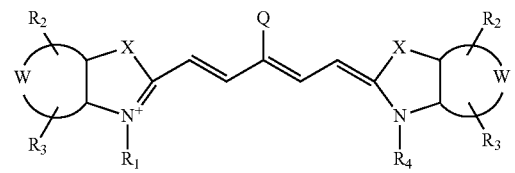

(2)

wherein X is independently selected from $C(CH_2Y_1)(CH_2Y_2)$, O, S, Se; and $Y_1$ and $Y_2$ are independently selected from H and $C_1$-$C_{20}$ alkyl that is linear or branched, saturated or unsaturated, optionally containing N, S, O in various forms; W represents non-metal atoms required to form a benzo-condensed, a naphtho-condensed or a pyrido-condensed ring. $R_1$ is selected from the group consisting of H, $(CH_2)_nCH_3$, $(CH_2)_nSO_3^-$ and $(CH_2)_nSO_3H$, wherein n is an integer selected from 0 to 6 when $R_1$ is $(CH_2)_nCH_3$, and n is an integer selected from 2 to 6 when $R_1$ is $(CH_2)_nSO_3^-$ or $(CH_2)_nSO_3H$. $R_4$ is selected from the group consisting of H, $(CH_2)_nCH_3$, $(CH_2)_nSO_3^-$ and $(CH_2)_nSO_3H$, wherein n is an integer selected from 0 to 6 when $R_4$ is $(CH_2)_nCH_3$, and n is an integer selected from 2 to 6 when $R_4$ is $(CH_2)_nSO_3^-$ or $(CH_2)_nSO_3H$. $R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety. Q is selected from a group consisting of a carboxyl functionalized nitrogen containing heterocyclic ring. Q is selected from a group consisting of a carbonyl functionalized nitrogen containing 6-membered heterocyclic ring, such as pyridine. Q is selected from a group consisting of isonicotinic acid, nicotinic acid and picolinic acid. Q is selected from the groups shown:

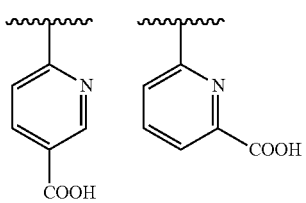

Herein, the carboxyl group is also in the form of an ester, an activated ester or carbonyl halide that is capable of reacting with nucleophiles. The carboxyl group is also in a form selected from the group CO-Obenzotriazolyl, CO—O—N-succinimidyl, CO-Otetrafluorophenyl, CO-Opentafluorophenyl, CO-Oimidazolyl, CO-Op-nitrophenyl.

Such molecules of formula (2) are chemically linked to biocompatible fluorescent molecules for a variety of applications including in vivo imaging.

In another embodiment the present invention is directed to a compound represented by formulae (2) or a salt thereof, wherein:

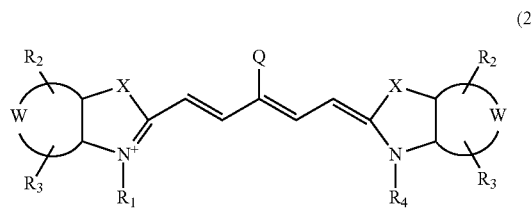

(2)

wherein X is independently selected from $C(CH_2Y_1)(CH_2Y_2)$, O, S, Se; and $Y_1$ and P $Y_2$ are independently selected from H and $C_1$-$C_{20}$ alkyl that is linear or branched, saturated or unsaturated, optionally containing N, S, O in various forms; W represents non-metal atoms required to form a benzo-condensed, a naphtho-condensed or a pyrido-condensed ring. $R_1$ is selected from the group consisting of H, $(CH_2)_nCH_3$, $(CH_2)_nSO_3^-$ and $(CH_2)_nSO_3H$, wherein n is an integer selected from 0 to 6 when $R_1$ is $(CH_2)_nCH_3$, and n is an integer selected from 2 to 6 when $R_1$ is $(CH_2)_nSO_3^-$ or $(CH_2)_nSO_3H$. $R_4$ is selected from the group consisting of $(CH_2)_nCH_3$, $(CH_2)_nSO_3^-$ and $(CH_2)_nSO_3H$, wherein n is an integer selected from 0 to 6 when $R_4$ is $(CH_2)_nCH_3$, and n is an integer selected from 2 to 6 when $R_4$ is $(CH_2)_nSO_3^-$ or $(CH_2)_nSO_3H$. $R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety. Q is selected from a group consisting of a carboxyl functionalized nitrogen containing heterocyclic ring. Q is selected from a group consisting of a carbonyl functionalized nitrogen containing 6-membered heterocyclic ring, such as pyridine. Q is selected from a group consisting of isonicotinic acid, nicotinic acid and picolinic acid. Q is selected from the groups shown:

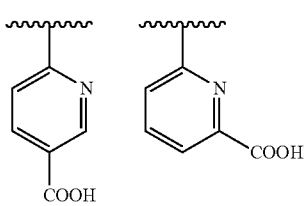

Herein, the carboxyl group is also in the form of an ester, an activated ester or carbonyl halide that is capable of reacting with nucleophiles. The carboxyl group is also in a form selected from the group CO-Obenzotriazolyl, CO—O—N-succinimidyl, CO-Otetrafluorophenyl, CO-Opentafluorophenyl, CO-Oimidazolyl, CO-Op-nitrophenyl.

Such molecules of formula (2) are chemically linked to biocompatible fluorescent molecules for a variety of applications including in vivo imaging.

In one embodiment for structural formula (2) Q is selected from a group consisting of a heteroaryl ring substituted with a carboxyl or 6-membered heteroaryl ring substituted with a carbonyl group.

In certain embodiments:
a) the carboxyl substituent on Q is selected from the group consisting of an ester, an activated ester; or
b) the carboxyl substituent on Q is selected from the group consisting of CO-Obenzotriazolyl, CO-ON-succinimidyl, CO-Otetrafluorophenyl, CO-Opentafluorophenyl, CO-Oimidazolyl, and CO-Op-nitrophenyl; and
c) the carbonyl substituent on Q is in the form of a carbonyl halide.

In another embodiments, Q is a carboxyl substituted nitrogen containing heterocyclic ring.

In another embodiments, Q is selected from the group consisting of carboxyl substituted pyridine, pyrimidone, pyrazine, and pyridazine.

In another embodiments, Q is carboxyl substituted pyridine.

In another embodiments, Q is selected from a group consisting of isonicotinic acid, nicotinic acid and picolinic acid.

In another embodiments, Q is represented by a structural formula selected from a group consisting of:

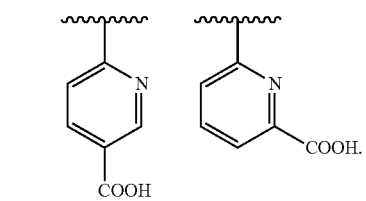

In another embodiments, Q is a carbonyl substituted nitrogen containing 6-membered heteroaryl ring In another embodiments, Q is a carbonyl substituted pyridine.

In the immediately preceding nine embodiments, the terms heterocyclic ring and heteroaryl ring both refer to heteroaryl ring as defined herein, such as pyridine.

In another embodiment, the present invention provides compounds representing $Z^1$-(PML)-$Z^2$ by the formula (2):

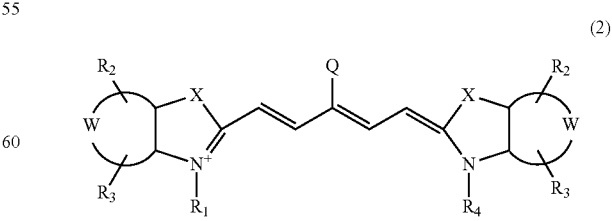

(2)

wherein, W represents non-metal atoms required to form a benzo-condensed, a naphtho-condensed or a pyrido-condensed ring.

In one aspect W represents the atoms necessary to form one to two fused aromatic rings having 6 atoms in each ring, which atoms are selected from —CH, —C, —CR$_7$, and —NR$_8$, where R$_8$ is 0 or 1 (such that each ring nitrogen is either quaternized or not), and each R$_7$ independently contains sulfo, trifluoromethyl, or halogen; R$_5$ independently contains a C$_1$-C$_8$ alkyl, in turn containing independently an H, amino or sulfo.

Incorporation of one or more non-hydrogen substituents on the fused rings can be used to tune the absorption and emission spectrum of the resulting dye.

Selected examples of the basic structure of Z$^1$ and Z$^2$ are shown below. These basic structures (3-6) are optionally further substituted as described in this section.

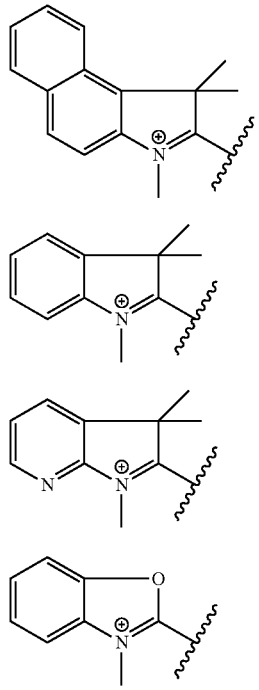

(3)

(4)

(5)

(6)

In one embodiment, X is independently selected from O, S, Se, —C(CH$_2$Y$_1$)(CH$_2$Y$_2$), wherein Y$_1$ and Y$_2$ are independently selected from H and C$_1$-C$_{20}$ alkyl that is linear or branched, saturated or unsaturated, optionally containing N, S, O in various forms, In another embodiment Y$_1$ and Y$_2$ together are part of a cyclic ring; or X is independently selected from —CR$_5$R$_6$, wherein R$_5$ and R$_6$, which may be the same or different, are alkyl, cycloalkyl, or arylalkyl, together part of a cyclic system and optionally further substituted.

In one aspect of the invention, R$_2$ and R$_3$ taken in combination complete a five or six-membered ring.

The substituent R$_1$ is typically selected from the group consisting of (CH$_2$)$_n$CH$_3$, (CH$_2$)$_n$SO$_3^-$ and (CH$_2$)$_n$SO$_3$H, wherein n is an integer selected from 0 to 6 when R$_1$ is (CH$_2$)$_n$CH$_3$, and n is an integer selected from 2 to 6 when R$_1$ is (CH$_2$)$_n$SO$_3^-$ or (CH$_2$)$_n$SO$_3$H. In one aspect, R$_1$ is (CH$_2$)$_3$SO$_3^-$ or (CH$_2$)$_4$SO$_3^-$ or CH$_2$CH$_3$. In one aspect of the invention R$_1$ is a substituent containing an aryl sulfonate or an amino group or a phthalimido group.

The substituent R$_1$ is typically selected from the group consisting of H, (CH$_2$)$_n$CH$_3$, (CH$_2$)$_n$SO$_3^-$ and (CH$_2$)$_n$SO$_3$H, wherein n is an integer selected from 0 to 6 when R$_1$ is (CH$_2$)$_n$CH$_3$, and n is an integer selected from 2 to 6 when R$_1$ is (CH$_2$)$_n$SO$_3^-$ or (CH$_2$)$_n$SO$_3$H. In one aspect, R$_1$ is (CH$_2$)$_3$SO$_3^-$ or (CH$_2$)$_4$SO$_3^-$ or CH$_2$CH$_3$. In one aspect of the invention R$_1$ is a substituent containing an aryl sulfonate or an amino group or a phthalimido group.

The substituent R$_4$ is typically selected from the group consisting of (CH$_2$)$_n$CH$_3$, (CH$_2$)$_n$SO$_3^-$ and (CH$_2$)$_n$SO$_3$H, wherein n is an integer selected from 0 to 6 when R$_4$ is (CH$_2$)$_n$CH$_3$, and n is an integer selected from 2 to 6 when R$_4$ is (CH$_2$)$_n$SO$_3^-$ or (CH$_2$)$_n$SO$_3$H. In one aspect, R$_4$ is (CH$_2$)$_3$SO$_3^-$ or (CH$_2$)$_4$SO$_3^-$ or CH$_2$CH$_3$. In one aspect of the invention R$_4$ is a substituent containing an aryl sulfonate or an amino group or a phthalimido group.

The substituent R$_4$ is typically selected from the group consisting of H, (CH$_2$)$_n$CH$_3$, (CH$_2$)$_n$SO$_3^-$ and (CH$_2$)$_n$SO$_3$H, wherein n is an integer selected from 0 to 6 when R$_4$ is (CH$_2$)$_n$CH$_3$, and n is an integer selected from 2 to 6 when R$_4$ is (CH$_2$)$_n$SO$_3^-$ or (CH$_2$)$_n$SO$_3$H. In one aspect, R$_4$ is (CH$_2$)$_3$SO$_3^-$ or (CH$_2$)$_4$SO$_3^-$ or CH$_2$CH$_3$. In one aspect of the invention R$_4$ is a substituent containing an aryl sulfonate or an amino group or a phthalimido group.

The substituents R$_2$ and R$_3$ are independently selected from the group H, halogens, carboxylate, carboxylic acid, carboxylic esters, amino, amide, alkyl or aryl sulfonamide, hydroxy, alkoxy, aryloxy, sulfate, cyano, nitro, azido, alkylamino, dialkylamino, trialkylammonium, phosphate, phosphate ester, phosphonate, sulphonic acid and a sulphonate moiety. In certain embodiments, R$_2$ and R$_3$ are independently, sulphonic acid or a salt thereof.

In one aspect of the invention, R$_2$ and R$_3$ could imply per-substitution, as in per-fluorinated W. Per-fluorination or poly-fluorination call lead to enhancement of fluorescence quantum yield.

As used herein "enhancement" means an increase in the fluorescence quantum yield, by about 5%, about 10%, about 15%, about 25%, about 50%, about 80%, about 90% about 95% about 98% about 99% about 100%.

In one aspect of the invention, the formula Z$^1$-(PML)-Z$^2$ is represented according to the formula (7):

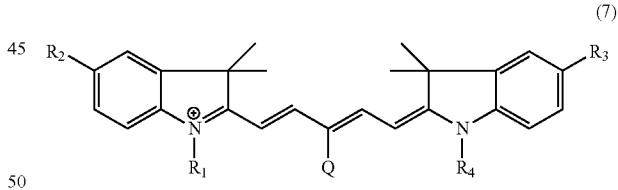

(7)

In one aspect of the invention, the compounds of the invention are sulfonated one or more times. If the compound of the invention is substituted by sulfo, it is typically sulfonated at R$_2$ or R$_3$ or both, (that is, for example, R$_2$ and/or R$_3$ are a sulfonic acid moiety, sulfonate moiety or sulfonamamide) or sulfoalkylated at R$_1$ or R$_4$ or both (that is, for example, R$_1$ and/or R$_4$ are (CH$_2$)$_n$SO$_3^-$ or (CH$_2$)$_n$SO$_3$H), or is both sulfonated and sulfoalkylated. In a particular embodiment, the compounds are are sulfonated up to three times (at positions corresponding to R$_2$ and R$_3$, and as sulfoalkyl at one of R$_1$ or R$_4$), leaving one of R$_1$ or R$_4$ for the location of a reactive group.

As used herein the terms sulfonic acid and (CH$_2$)$_n$SO$_3$H or a sulfonate group and (CH$_2$)$_n$SO$_3^-$ can be used interchangeably. However in certain embodiments the terms a sulfonic acid moiety, sulfonate moiety or sulfonamide refer to substituents which are attached to the remainder of the molecule by the a sulfonic acid moiety, sulfonate moiety or sulfonamamide moiety, ie., —SO$_2$NR'R"

In certain embodiments, at least one of R$_1$ to R$_3$ is or contains a sulphonic acid moiety or a sulphonate moiety. In certain embodiments, at least one of R$_1$ to R$_3$ is a sulphonic acid moiety or a sulphonate moiety.

In certain embodiments, R$_1$ and R$_4$ are independently (CH$_2$)$_n$SO$_3^-$ or (CH$_2$)$_n$SO$_3$H.

In one embodiment of the present invention the compounds are sulfonated up to four times (at R$_2$ and R$_3$, and as sulfoalkyl at R$_1$ and R$_4$). In another embodiment of the present invention the compounds are sulfonated at least four times (at R$_2$ and R$_3$, and as sulfoalkyl at R$_1$ and R$_4$). In another embodiment of the present invention, any reactive group (or chemically linked molecule) can be attached at Q, in addition the compounds of the present invention being sulfonated up to four times (at R$_2$ and R$_3$, and as sulfoalkyl at R$_1$ and R$_4$). In another embodiment of the present invention, any reactive group (or chemically linked molecule) can be attached at Q, in addition the compounds of the present invention being sulfonated at least four times (at R$_2$ and R$_3$, and as sulfoalkyl at R$_1$ and R$_4$). This extra sulfonation, as well as the change in attachment site, results in reactive dyes and dye conjugates that are brighter, more soluble in aqueous solutions, and more resistant to the fluorescence quenching that results from dye-dye stacking interactions.

In one aspect of the invention, the formula Z$^1$-(PML)-Z$^2$ is represented according to the formula (8):

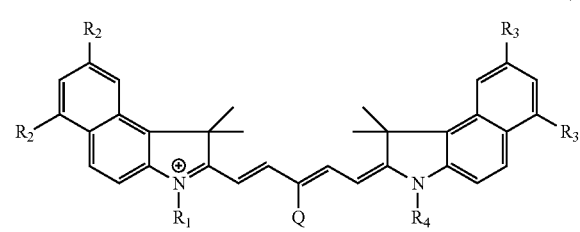

(8)

In one aspect of the invention, the compounds of the invention that are sulfonated one or more times are typically sulfonated at R$_2$ or R$_3$, or sulfoalkylated at R$_1$ or R$_4$ or both, or is both sulfonated and sulfoalkylated. In particular, the compounds of the present invention are sulfonated up to four times leaving one of R$_1$ or R$_4$ for the location of a reactive group.

In one embodiment of the present invention the compounds are sulfonated up to six times (at R$_2$ and R$_3$, and as sulfoalkyl at R$_1$ and R$_4$). In another embodiment of the present invention the compounds are sulfonated at least six times (at R$_2$ and R$_3$, and as sulfoalkyl at R$_1$ and R$_4$). In another embodiment of the present invention, any reactive group (or chemically linked molecule) can be attached at Q, in addition the compounds of the present invention being sulfonated up to six times (at R$_2$ and R$_3$, and as sulfoalkyl at R$_1$ and R$_4$). In another embodiment of the present invention, any reactive group (or chemically linked molecule) can be attached at Q, in addition the compounds of the present invention being sulfonated at least six times (at R$_2$ and R$_3$, and as sulfoalkyl at R$_1$ and R$_4$). This extra sulfonation, as well as the change in attachment site, results in reactive dyes and dye conjugates that are brighter, more soluble in aqueous solutions, and more resistant to the fluorescence quenching that results from dye-dye stacking interactions.

In one embodiment, the PML moiety has the formula (9):

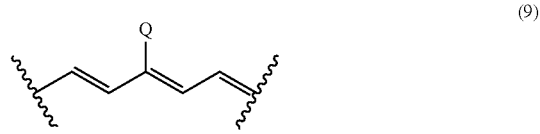

(9)

wherein Q is selected from a group consisting of carboxyl functionalized heterocyclic ring (heteroaryl substituted with a carboxy group). In this embodiment, heterocyclic ring and heteroaryl ring refers to heteroaryl ring as defined herein, such as pyridine and functionalized refers to substituted.

Suitable examples of appropriate PML moieties for compounds of the present invention (carbocyanine dyes) have been described in the literature, including PML moieties that incorporate nonhydrogen substituents, ring structures, and rigidizing elements (U.S. Pat. No. 5,831,098 to Ollmann, Jr (1998); U.S. Pat. No. 6,086,737 to Patonay et al. (2000); U.S. Pat. No. 6,048,982 to Waggoner (2000); and U.S. Pat. No. 5,453,505 to Lee et al. (1995); U.S. Pat. No. 5,639,874 to Middendorf et al. (1997); U.S. Pat. No. 3,864,644 to Lincoln et al (1975); U.S. Pat. No. 4,011,086 to Simson (1977); U.S. Pat. No. 6,747,159 to Caputo (2004); all incorporated herein by reference in their entirety).

In one embodiment the invention is directed to a PML of the formula (9), wherein Q is selected from a group consisting of a functionalized nitrogen-containing heterocyclic ring. One aspect of the invention is a PML of the formula (9), wherein Q is selected from a group consisting of a substituted nitrogen-containing heteroaryl ring. In these embodiments, heterocyclic ring and heteroaryl ring refers to heteroaryl ring as defined herein, such as pyridine, and functionalized refers to substituted.

In one embodiment of the invention, Q contains at least one substituent which is a reactive group that is attached to the heterocyclic (heteroaryl) ring (Q) by a covalent linkage. In one embodiment the compounds of the present invention which contain a reactive group label a wide variety of organic or inorganic substances that contain or are modified to contain functional groups with suitable reactivity, resulting in chemical attachment of the compounds of the present invention to form a conjugated substance.

As used herein, "reactive group" means a moiety on a compound of the present invention or that can be added to a compound of the present invention that is capable of chemically reacting with a functional group on a different compound to form a covalent linkage, or a moiety on a different compound that is capable of chemically reacting with a functional group on compound of the present invention to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the compound of the present invention and the substance to be conjugated results in one or more atoms of the reactive group to be incorporated into a new linkage attaching the dye to the conjugated substance.

One aspect of the invention is a PML of the formula (9), wherein Q is selected from a group consisting of carboxyl functionalized nitrogen containing heterocyclic ring (heteroaryl substituted with carboxyl). In this embodiment, heterocyclic ring and heteroaryl ring refers to heteroaryl ring as defined herein, such as pyridine and functionalized refers to substituted.

In one aspect of the invention PML is of the formula (9), wherein Q is selected from a group consisting of carboxyl functionalized nitrogen containing 6-membered heterocyclic ring (heteroaryl substituted with carboxyl), such as pyridine, pyrimidone, pyrazine, and pyridazine. (heteroaryl substituted with carboxyl). In this embodiment, heterocyclic ring and heteroaryl ring refers to heteroaryl ring as defined herein, such as pyridine and functionalized refers to substituted.

Another aspect of the invention is a PML of the formula (9), wherein Q is selected from a group consisting of carboxyl functionalized nitrogen containing 6-membered heterocyclic ring, (heteroaryl substituted with carboxyl), such as pyridine. (heteroaryl substituted with carboxyl). In this embodiment, heterocyclic ring and heteroaryl ring refers to heteroaryl ring as defined herein, such as pyridine and functionalized refers to substituted.

In another aspect of the invention PML is of the formula (9), wherein Q is selected from a group consisting of nicotinic acid and picolinic acid or a salt thereof.

In one aspect of the invention is a PML of the formula (9), wherein Q is selected from the groups shown:

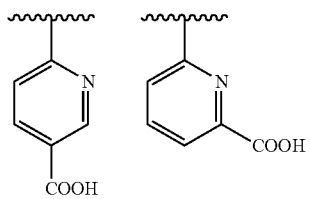

or a salt thereof.

In another aspect of the invention is a PML of the formula (9), wherein Q is selected from the groups shown:

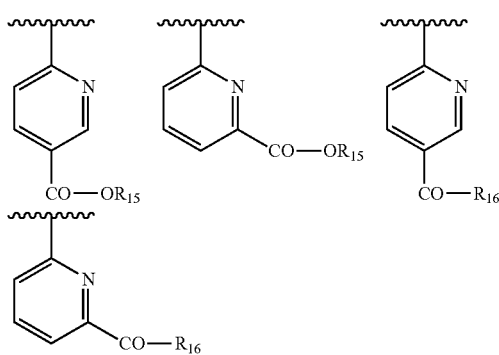

wherein, the carboxyl group is also in the form of an activated ester ($R_{15}$) or carbonyl halide ($R_{16}$=F, Cl, Br) that is capable of reacting with nucleophiles. The carboxyl group CO-OR$_{15}$ is also in a form selected from the group CO-Obenzotriazolyl, CO-ON-hydroxysuccinimidyl, CO-Otetrafluorophenyl, CO-Opentafluorophenyl, CO-Oimidazolyl, CO-Op-nitrophenyl.

The PML moiety typically originates from the coupling agent used in the synthesis of a compound of the present invention. For example, N,N'-diphenylformamidine and triethylorthoformate yields PML moieties. Malonaldehyde bis (phenylimine) hydrochloride, 1,1,3-trimethoxypropane, and 1,1,3,3-tetramethoxypropane and glutaconaldehyde dianil monochloride also yield PML moieties (dyes).

In one aspect of the invention, the PML moiety is introduced into the dye using the malonodialdehydes moieties shown below:

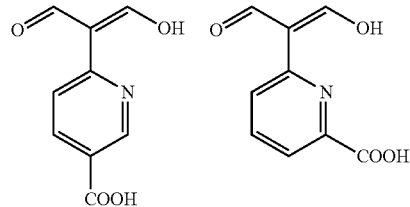

Accordingly, the present invention provides compounds representing $Z^1$ (PML)-$Z^2$ by the formula (2):

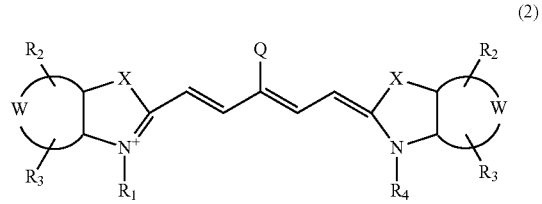

(2)

wherein $R_1$ is $(CH_2)_nSO_3^-$ or $(CH_2)_nSO_3H$.

In one aspect the present invention, is directed to compounds having any of the formulae (10-11):

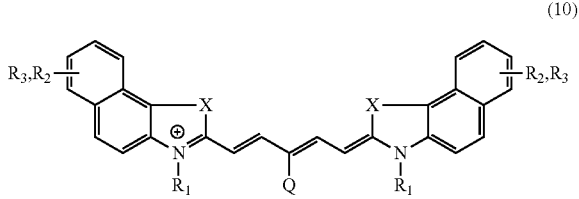

(10)

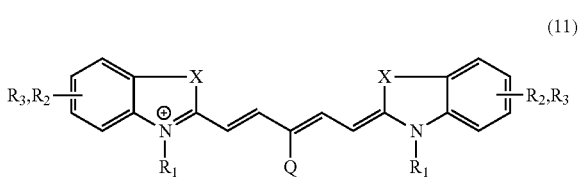

(11)

In another aspect the present invention is directed to compounds having any of the formulae (12-15):

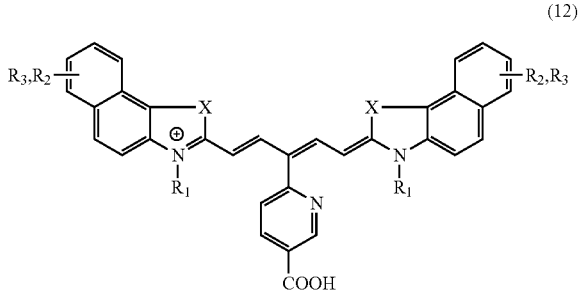

(12)

-continued (13)

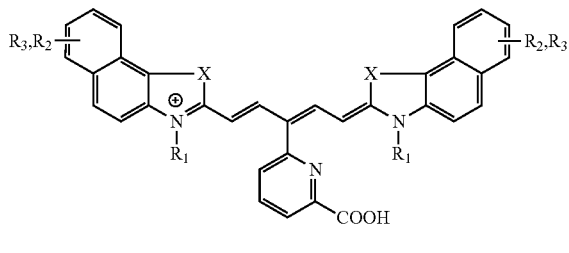

(14)

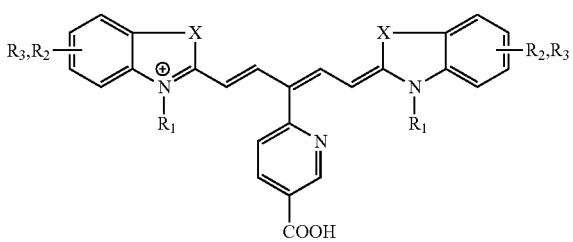

(15)

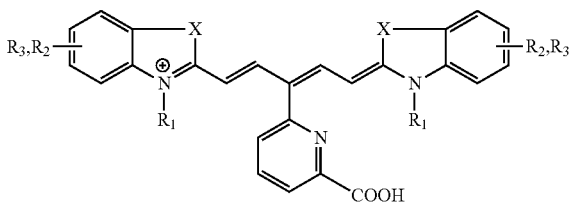

In one aspect of the invention when Q is or contains an activated ester, the compound can be chemically linked to bifunctional linkers such as aminoethylmaleimide, aminopropylmaleimide, aminopropylazide, aminopropylthiol, mercaptoethylamine, propargylamine 3-aminopropanol, diaminopropane, and diaminobutane to provide additional reactive functional groups in a suitable solvent under neutral or basic conditions.

In one aspect of the invention when Q is or contains $NH_2$, the compound of the invention can be chemically linked to bifunctional linkers such as propargylic acid, succinimidylpyridinedithiopropionate, maleimide-PEG-N-hydroxysuccinimide ester to provide additional reactive functional groups in a suitable solvent under neutral or basic conditions.

When a compound of the invention is depicted herein by structure indicating the positions of the double bonds in the rings an polymethine linker, it is to be understood that the structure also encompasses any resonance structures as shown, for example, in the FIGURE below:

In one embodiment, the present invention provides compounds representing $Z^1$-(PML-BM)-$Z^2$ by the formula (16):

(16)

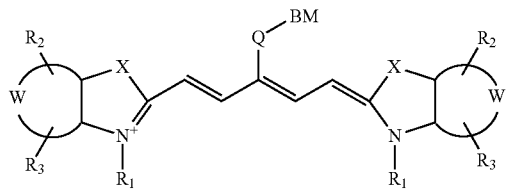

wherein BM a biomolecule chemically linked via Q residing on the PML.

In one aspect BM is a moiety that changes or alters or enhances accumulation, biodistribution, elimination, targeting, binding, and/or recognition of the compounds (fluorochromes) of the general structure $Z^1$-(PML)-$Z^2$. BMs include but are not limited to antibodies and fragments thereof, proteins, peptides, amino acids, antibodies (or antigen-binding antibody fragments, such as single chain antibodies), glycoproteins, ligands for cell receptors, polysaccharides, nucleosides, aptamers, cell receptors themselves, enzyme substrates, enzyme cofactors, biotin, hormones, neurohormones, neurotransmitters, growth factors, cytokines, lymphokines, lectins, selectins, toxins, and carbohydrates. Other targeting and delivery approaches using various biomolecules can also be used, such as folate-mediated targeting (Leamon & Low, *Drug Discovery Today*, 6:44-51, 2001), transferrin, vitamins, carbohydrates and ligands that target internalizing receptors, including, but not limited to, asialoglycoprotein receptor, somatostatin, nerve growth factor, oxytocin, bombesin, calcitonin, arginine vasopressin, angiotensin II, atrial natriuretic peptide, insulin, glucagons, prolactin, gonadotropin, various opioids and urokinase-type plasminogen activator. Also included are membrane, transmembrane, and nuclear translocation signal sequences, which can be derived from a number of sources including, without limitation, viruses and bacteria. BM can also be an organic molecule, polymer, dendrimer, drug, lipid, lipid assembly, therapeutic drug molecules, polymeric microparticle, cells, or a nanoparticle. In certain embodiments, BMs can also include small molecule drugs, phototherapeutic molecules and derivatives thereof.

In certain embodiments of the present invention, when BM is chemically linked to a compound of the present invention the fluorescence of the compound of the present invention is enhanced. In certain embodiments the fluorescence is enhanced by about 10%, about 25%, about 50% or more than about 50% which compared with the unlinked compound.

In one aspect of the invention several copies of BM are chemically linked to Q via multivalent linkers or linkers containing several reactive functional groups to form a biocompatible fluorescent molecule of the structure $(Z^1$-(PML)-$Z^2)$-$((L)_w$-$(BM)q)t$, wherein L is a linker or multivalent linker, and t=1-6, w=1-500 and q=1-500. $(L)_w$ represents copies of the same linker or a combination of different linkers. Suitbale

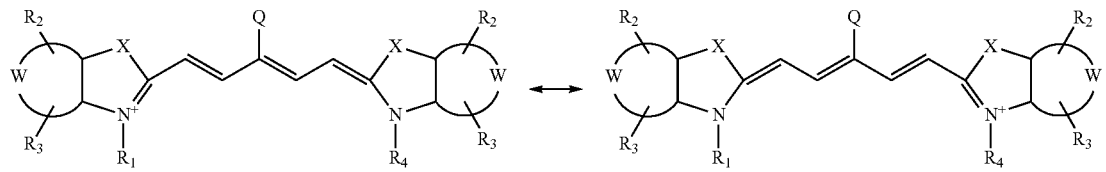

linkers include but are not limited to aminocaproic acid, glutamic acid, and poly-glutamic acid.

In another aspect of the invention, more than one compound (fluorochrome) of the structure $Z^1$-(PML)-$Z^2$ can be chemically linked to a single BM to form a biocompatible fluorescent molecule of the structure $[Z^1$-(PML)-$Z^2]_k$-BM, wherein k=1-500.

In one embodiment $Z^1$-(PML-BM)-$Z^2$ is a biocompatible fluorescent molecule wherein the compound has an absorption and emission maxima between about 440 and about 1100 nm, between about 550 and about 800 nm, between about 500 and about 900 nm or between about 600 and about 900 nm.

In one embodiment the compounds (fluorochromes) and biocompatible fluorescent molecules of the present invention are activated after target interaction. "Activated after target interaction" is meant a change that alters a detectable property, e.g., an optical property, of the fluorochromes or biocompatible fluorescent molecules. This includes, but is not limited to, a modification, alteration, or binding (covalent or non-covalent) that results in a detectable difference in properties, e.g., optical properties of the fluorochromes or biocompatible fluorescent molecules, e.g., changes in the fluorescence signal amplitude (e.g., dequenching and quenching), change in wavelength, fluorescence lifetime, spectral properties, or polarity. In another embodiment, a quencher molecule is used to quench the fluorescent signal of the biocompatible fluorescent molecules. By adopting these activated and unactivated states, it is therefore possible to determine whether the fluorochrome or biocompatible fluorescent molecule is active or inactive in a subject by identifying a change in the signal intensity. In addition, the fluorochromes and biocompatible fluorescent molecules can be designed such that the they exhibit little or no signal until activated. Activation can be, without limitation, by enzymatic cleavage, enzymatic conversion, phosphorylation or dephosphorylation, conformation change due to binding, enzyme-mediated splicing, enzyme-mediated transfer, hybridization of complementary DNA or RNA, analyte binding, such as association with an analyte such as $Na^+$, $K^+$, $Ca^{2+}$, $Cl^-$, or another analyte, change in hydrophobicity of the environment and chemical modification.

In one embodiment the compounds (fluorochromes) and biocompatible fluorescent molecules of the present invention have a high binding affinity to a target.

Also provided herein is a method of in vivo optical imaging, the method comprising (a) administering to a subject a compound (fluorochrome) or biocompatible fluorescent molecule of the present invention; (b) allowing time for the compound (fluorochrome) or biocompatible fluorescent molecule to distribute within the subject or to contact or interact with a biological target; (c) illuminating the subject with light of a wavelength absorbable by the compound (fluorochrome) or biocompatible fluorescent molecule; and (d) detecting the optical signal emitted by the compound (fluorochrome) or biocompatible fluorescent molecule.

The optical signal generated by the compounds (fluorochromes) or biocompatible fluorescent molecules of the present invention, whether collected by tomographic, reflectance, planar, endoscopic, microscopic, surgical goggles, video imaging technologies, or other methods such as microscopy including intravital and two-photon microscopy, and whether used quantitatively or qualitatively, is also considered to be an aspect of the invention.

One aspect of the invention is a method wherein the presence, absence, distribution, or level of optical signal emitted by the compound (fluorochrome) or biocompatible fluorescent molecule is indicative of a disease state.

The invention also features a method of using the compounds (fluorochromes) and biocompatible fluorescent molecules of the present invention to detect an abnormality in a patient or subject, e.g., any abnormality associated with a disease such as cancer, a cardiovascular disease, AIDS, a neurodegenerative disease, an inflammatory disease, a respiratory disease, a metabolic disease, a bone disease or an immunologic disease. The invention also features a method of assessing the effect of a compound or therapy on a specified molecular target by using the compounds (compositions) of the present invention, wherein the subject is imaged prior to and after treatment with the compound or therapy, and the corresponding images are compared.

The imaging method steps of the present invention can also be repeated at predetermined intervals thereby allowing for the evaluation of emitted signal of the $Z^1$-(PML)-$Z^2$ containing compound in a subject or sample over time. The emitted signal may take the form of an image. The subject may be a vertebrate animal, for example, a mammal, including a human. The animal may also be non-vertebrate, (e.g., *C. elegans, drosophila*, or other model research organisms, etc.). The sample can include, without limitation, cells, cell culture, tissue sections, organs, organ sections, cytospin samples, or the like.

The invention also features an in vivo method for selectively detecting and imaging two or more $Z^1$-(PML)-$Z^2$ containing compounds simultaneously. The method comprises administering to a subject two or more $Z^1$-(PML)-$Z^2$ containing compounds, either at the same time or sequentially, whose optical properties are distinguishable. The method therefore allows the recording of multiple events or targets.

The invention also features an in vivo method for selectively detecting and imaging one or more $Z^1$-(PML)-$Z^2$ containing compounds, simultaneously with one or more targeted or activatable optical imaging probes, or in a dual imaging protocol with magnetic resonance imaging, computed tomography (CT), X-ray, ultrasound, or nuclear medicine imaging modalities and their respective imaging agents. The method comprises administering to a subject one or more imaging probes, either at the same time or sequentially, including at least one $Z^1$-(PML)-$Z^2$ containing compound, whose properties are distinguishable from that of the others. In one aspect a dual imaging protocol is optical and magnetic resonance imaging using $Z^1$-(PML)-$Z^2$ containing compounds sequentially or nearly simultaneously with magnetic resonance imaging agents, (for example, iron oxide based agents or gadolinium based agents such as gadopentetate). The method therefore, allows the recording of multiple events or targets using more than one imaging modality or imaging agent.

In another aspect, the invention features an in vitro optical imaging method comprising contacting the sample with $Z^1$-(PML)-$Z^2$ containing compounds; allowing time for the probes to become activated or bind to a target of interest in the sample; optionally, removing the unbound probes; illuminating the target with light of a wavelength absorbable by the $Z^1$-(PML)-$Z^2$ containing compounds; and detecting the optical signal emitted by the $Z^1$-(PML)-$Z^2$ containing compounds.

After administration, detection can occur, for example, by in vitro methods, i.e., flow cytometry or by in vivo imaging methods, i.e., tomographic, catheter, planar/reflectance systems or endoscopic systems.

In one embodiment, the $Z^1$-(PML)-$Z^2$ containing compounds derived thereof) can be used to label a sample ex vivo. The sample, e.g., cells, can be derived directly from a subject or from another source (e.g., from another subject, cell culture etc.). The $Z^1$-(PML)-$Z^2$ containing compound can be mixed with the cells to effectively label the cells (covalently or non-covalently) and the resulting labeled cells injected into a subject. This method can be used for monitoring trafficking and localization of certain cell types, including T-cells, tumor cells, immune cells, stem cells, and other cell types. In particular, this method may be used to monitor cell based therapies. The sample can also be derived from non-mammalian sources including but not limited to plants, insects, viruses, bacteria, and bacteriophage.

Another aspect of the invention features $Z^1$-(PML)-$Z^2$ containing compounds that can be used for in vivo imaging and labeling samples ex vivo, including cells, without the use of dimethylsulfoxide (DMSO) or other organic solvents (i.e. physiologic buffers or solutions) that are generally toxic to biological subjects or samples.

For labeling of BMs or cells, the compounds (fluorochromes) of the present invention can be incubated with BMs at various concentrations for about 5 minutes to 24 hours or more at about 4°-37° C. After the incubation the free or fluorochrome that has not been chemically linked to the BM can be removed, such as by chromatography or ultrafiltration methods that are well known in the art. For cells, after the incubation, the cells can be centrifuged to create a cell pellet from which the supernatant is removed. Cells can be resuspended in culture media or physiologic saline to wash away residual, unbound or free fluorochrome. This can be repeated several times. In this manner, cells can be labeled either by direct conjugation to internal or external cellular molecules or by non-specific cell uptake into various intracellular compartments, including but not limited to cytosol, endosomes, nucleus, golgi apparatus, and other intracellular organelles.

Another aspect of the invention features $Z^1$-(PML)-$Z^2$ containing compound containing imaging probes formulated in a pharmaceutical composition suitable for administration to animal, including human, subjects. The pharmaceutical composition can include the nanoparticles and one or more stabilizers in a physiologically acceptable (relevant) carrier.

Another aspect of the invention features biocompatible fluorescent $Z^1$-(PML)-$Z^2$ containing compounds formulated in pharmaceutical compositions suitable for administration to animal, including human, subjects and cells. The pharmaceutical composition can include one or more stabilizers in a physiologically acceptable (relevant) carrier.

Suitable examples of stabilizers for use in the methods of the present invention, include but are not limited to, low molecular weight carbohydrate, in one aspect it is a linear polyalcohol, such as sorbitol, and glycerol; or mannitol. Other low molecular weight carbohydrates, such as inositol, may also be used. Physiologically relevant carriers can include water, saline, and may further include agents such as buffers, and other agents such as preservatives that are compatible for use in pharmaceutical formulations.

The invention also features a method of gene sequence recognition using fluorescent $Z^1$-(PML)-$Z^2$ containing compounds, labeled nucleic acid recognition molecules, including DNA, RNA, modified nucleic acid, PNA, molecular beacons, aptamers, or other nucleic acid binding molecules (for example, small interfering RNA or siRNA). The method includes the use of one or more fluorescent $Z^1$ (PML)-$Z^2$ containing compounds, together with techniques such as hybridization, ligation, cleavage, recombination, synthesis, sequencing, mutation detection, real-time polymerase chain reactions, in situ hybridization, and the use of microarrays. For example, for detecting a single stranded nucleic acid (i.e., mRNA, cDNA or denatured double-stranded DNA) in a sample, via nucleic acid hybridization principles, a fluorescent $Z^1$-(PML)-$Z^2$ containing compound chemically linked to a single-stranded nucleic acid is contacted with a sample containing one or more single stranded nucleic acids and the fluorescence of the fluorescent $Z^1$-(PML)-$Z^2$ containing compound is detected, wherein the presence or level of fluorescence signal emitted by the fluorescent $Z^1$-(PML)-$Z^2$ containing compound indicates the presence or amount of nucleic acid in the sample.

The optical signal generated by the $Z^1$-(PML)-$Z^2$ containing compounds or derivatives thereof, whether collected by tomographic, reflectance, planar, endoscopic, microscopic, surgical goggles or imager, video imaging technologies, or other methods such as microscopy including intravital and two-photon microscopy, and whether used quantitatively or qualitatively, is also considered to be an aspect of the invention.

Another aspect of the invention features a kit, which includes the $Z^1$-(PML)-$Z^2$ containing compounds, and optionally, and instructions for using the fluorochromes or imaging probes for in vivo or in vitro imaging methods. The kit optionally may include components that aid in the use of the fluorochromes or imaging probes for the disclosed methods, such as buffers, and other formulating agents; alternatively, the kit may include medical devices that aid in the administration of the imaging probes to subjects.

The $Z^1$-(PML)-$Z^2$ containing compounds, and pharmaceutical compositions of the present invention can be administered orally, parentally, by inhalation, topically, rectally, nasally, buccally, vaginally, or via an implanted reservoir. The term "parental administration" includes intravenous, intramuscular, subcutaneous, intraarterial, intraarticular, intrasynovial, intrasternal, intrathecal, intraperitoneal, intracisternal, intrahepatic, intralesional, intracranial and intralymphatic injection or infusion techniques. The $Z^1$-(PML)-$Z^2$ containing compound can also be administered via catheters or through a needle to a tissue.

In one embodiment, an effective amount (which is an amount effective to cause or increase fluorescence) of the compounds of the present invention are administered. In one embodiment, between about 1 ng/kg and about 100 mg/kg, between about 100 ng/kg and 10 mg/kg, between about 1 μg/kg and about 5 mg/kg, between about 10 μg/kg and about 2 mg/kg, between about 50 μg/kg and about 1 mg/kg of the compound of the present invention is administered.

Preferred $Z^1$-(PML)-$Z^2$ containing compounds have the following properties: (1) high quantum yield (e.g., quantum yield greater than 5% in aqueous medium), (2) narrow emission spectrum (e.g., less than 75 nm; more preferably less than 50 nm), (3) spectrally separated absorption and emission spectra (e.g., separated by more than 20 nm; more preferably by more than 50 nm), (3) have high chemical stability and photostability (e.g., retain fluorescent properties after exposure to light), (4) are non toxic or minimally toxic to cells or subjects at doses used for imaging protocols, (as measured for example, by $LD_{50}$ or irritation studies, or other similar methods known in the art) and/or (5) have commercial viability and scalable production for large quantities (e.g., gram and kilogram quantities).

The compounds of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

The compounds of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propaanesulfonate, naphthalene-1-sulfonate, naphthalene-2-sulfonate, mandelate, and the like.

The term "alkyl" as used herein means a saturated straight-chain, branched or cyclic hydrocarbon. When straight-chained or branched, an alkyl group is typically C1-C20, more typically C1-C10; when cyclic, an alkyl group is typically C3-C12, more typically $C_3$-$C_7$. Examples of alkyl groups include methyl, ethyl, n-propyl, iso-propyl, n-butyl, sec-butyl and tert-butyl and 1,1-dimethylhexyl.

An "aliphatic group" is non-aromatic, and may optionally contain one or more units of unsaturation, e.g., double and/or triple bonds. An aliphatic group may be straight-chained or branched and typically contains between 1 and 12 carbon atoms, more typically between 1 and 6 carbon atoms, and even more typically between 1 and 4 carbon atoms. One or more methylene group in an aliphatic group can optionally be replaced by O, S, or NH.

As used herein the term non-aromatic carbocyclic ring or non-aromatic heterocyclic ring as used alone or as part of a larger moiety refers to a non-aromatic carbon or heteroatom containing ring which can be saturated or contain one or more units of unsaturation, having three to fourteen atoms including monocyclic and polycyclic rings in which the carbocyclic or heterocyclic ring can be fused to one or more non-aromatic carbocyclic or heterocyclic rings or one or more aromatic (carbocyclic or heterocyclic) rings.

The term "alkoxy" as used herein is represented by —OR, wherein R is an alkyl group as defined above.

The term "carbonyl" as used herein is represented by —C(═O)R, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or contain one or more units of unsaturation. Examples of heterocyclic groups include piperidinyl, piperizinyl, pyrrolidinyl, pyrazolidinyl, imidazolidinyl, tetrahydroquinolinyl, inodolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below. Preferably the nitrogen is unsubstituted.

A substituted aryl group as defined herein contains one or more substitutable ring atoms, such as carbon or nitrogen ring atoms. Examples of suitable substituents on a substitutable ring carbon atom of an aryl or aliphatic group include halogen (e.g., —Br, Cl, I and F), —OH, C1-C4 alkyl, C1-C4 haloalkyl, —NO₂, C1-C4 alkoxy, C1-C4 haloalkoxy, —CN, —NH₂, C1-C4 alkylamino, C1-C4 dialkylamino, —C(O)NH₂, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)₂, —NHC(O)O—(C1-C4 alkyl), —C(O)OH, —C(O)O—(C1-C4 alkyl), —NHC(O)NH₂, —NHC(O)NH(C1-C4 alkyl), —NHC(O)N(C1-C4 alkyl)₂, —NH—C(═NH)NH₂, —SO₂NH₂, —SO₂NH(C1-C3alkyl), —SO₂N(C1-C3alkyl)₂, NHSO$_2$H, NHSO$_2$(C1-C4 alkyl) and aryl. Preferred substituents on aryl groups are as defined throughout the specification.

Examples of suitable substituents on a substitutable ring nitrogen atom of an aryl group include C$_1$-C$_4$ alkyl, NH$_2$, C$_1$-C$_4$ alkylamino, C$_1$-C$_4$ dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3alkyl), —SO$_2$N(C1-C3alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, Substituted alkyl, aliphatic, non-aromatic carbocyclic or heterocyclic group as defined herein contain one or more substituents. Examples of suitable substituents for an alkyl group include those listed above for a substitutable carbon of an aryl and aliphatic and the following: =O, =S, =NNHR, =NN(R)$_2$, =NNHC(O)R, =NNHCO$_2$ (alkyl), =NNHSO$_2$ (alkyl), =NR, Spiro cycloalkyl group or fused cycloalkyl group. R** in each occurrence, independently is —H or C1-C6 alkyl. Preferred substituents on alkyl aliphatic, non-aromatic carbocyclic or heterocyclic group groups are as defined throughout the specification.

In vitro Testing and Use

The compounds (fluorochromes) and biocompatible fluorescent molecules of the present invention can be tested in vitro by one skilled in the art to assess its biological and performance characteristics. For instance, different types of cells grown in culture can be used to assess their biological and performance characteristics. Uptake, labeling, binding targeting or cellular localization of the fluorochromes and biocompatible fluorescent molecules can be assessed using techniques known in the art such as spectroscopy methods fluorescent microscopy, and flow cytometry. For example, the fluorochromes and biocompatible fluorescent molecules of the present invention can be contacted with a sample for a period of time and then washed to remove any free or unbound molecules. The sample can then be viewed using a fluorescent microscope equipped with appropriate filters matched to the optical properties of the fluorochromes and biocompatible fluorescent molecules of the present invention. Fluorescent microscopy of cells in culture is also a convenient means for determining whether uptake and binding occurs in one or more subcellular compartments. Tissues, tissue sections and other types of samples such as cytospin samples can also be used in a similar manner to assess the biological and performance characteristics of the molecules. Other fluorescent detection methods including, but not limited to flow cytometry, immunoassays, hybridization assays, and microarray analysis can also be used.

Optical Imaging

The general principles of fluorescence, optical image acquisition, and image processing can be applied in the practice of the invention. For a review of optical imaging techniques, see, e.g., Alfano et al., *Ann. NY Acad. Sci.* 820:248-270, 1997.

An imaging system useful in the practice of this invention typically includes three basic components: (1) an appropriate light source for fluorochrome and biocompatible fluorescent molecule excitation, (2) a means for separating or distinguishing emissions from light used for the excitation, and (3) a detection system to detect the optical signal emitted.

In general, the optical detection system can be viewed as including a optical gathering/image forming component and a optical detection/image recording component. Although the optical detection system can be a single integrated device that incorporates both components, the optical gathering/image forming component and light detection/image recording component will be discussed separately.

A particularly useful optical gathering/image forming component is an endoscope. Endoscopic devices and techniques which have been used for in vivo optical imaging of numerous tissues and organs, including peritoneum (Gahlen et al., *J Photochem. Photobiol. B* 52:131-135, 1999), ovarian cancer (Major et al., *Gynecol. Oncol.* 66:122-132, 1997), colon and rectum (Mycek et al., *Gastrointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et al., *Urol. Int.* 63:27-31, 1999; and Riedl et al., *J Endourol.* 13:755-759, 1999), lung (Hirsch et al., *Clin Cancer Res* 7:5-220, 2001), brain (Ward, *J Laser Appl.* 10:224-228, 1998), esophagus, and head and neck regions can be employed in the practice of the present invention.

Other types of optical gathering components useful in the invention are catheter-based devices, including fiber optics devices. Such devices are particularly suitable for intravascular imaging. See, e.g., Tearney et al., *Science* 276:2037-2039, 1997; and *Circulation* 94:3013, 1996.

Still other imaging technologies, including phased array technology (Boas et al., *Proc. Natl. Acad. Sci. USA* 91:4887-4891, 1994; Chance, *Ann. NY Acad. Sci.* 838:29-45, 1998), optical tomography (Cheng et al., *Optics Express* 3:118-123, 1998; and Siegel et al., *Optics Express* 4:287-298, 1999), intravital microscopy (Dellian et al., *Br. J. Cancer* 82:1513-1518, 2000; Monsky et al, *Cancer Res.* 59:4129-4135, 1999; and Fukumura et al., *Cell* 94:715-725, 1998), confocal imaging (Korlach et al., *Proc. Natl. Acad. Sci. USA* 96:8461-8466, 1999; Rajadhyaksha et al., *J. Invest. Dermatol.* 104:946-952, 1995; and Gonzalez et al., *J. Med.* 30:337-356, 1999) and fluorescence molecular tomography (FMT) (Nziachristos et al., *Nature Medicine* 8:757-760, 2002; U.S. Pat. No. 6,615, 063, PCT Application No. WO 03/102558, and PCT US/03/07579) can be employed in the practice of the present invention, the IVIS® Imaging System (Xenogen, Alameda, Calif.), Maestro (CRI, Woburn, Mass.) the SoftScan® and the eXplore Optix™ (Advanced Research Technologies, Montreal, Canada) system can be employed in the practice of the present invention.

A suitable optical detection/image recording component, e.g., charge coupled device (CCD) systems or photographic film, can be used in the invention. The choice of optical detection/image recording will depend on factors including type of optical gathering/image forming component being used. Selecting suitable components, assembling them into an optical imaging system, and operating the system is within ordinary skill in the art.

Diagnostic and Disease Applications and Methods

The methods of the invention can be used to determine a number of indicia, including tracking the localization of the fluorochromes and biocompatible fluorescent molecules in the subject over time or assessing changes or alterations in the metabolism and/or excretion of the molecules in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The invention can be used to help a physician or surgeon to identify and characterize areas of disease, such as arthritis, cancers and specifically colon polyps, or vulnerable plaque, to distinguish diseased and normal tissue, such as detecting tumor margins that are difficult to detect using an ordinary operating microscope, e.g., in brain surgery, help dictate a therapeutic or surgical intervention, e.g., by determining whether a lesion is cancerous and should be removed or non-cancerous and left alone, or in surgically staging a disease, e.g., intraoperative lymph node staging, sentinel lymph node mapping, or assessing intraoperative bleeding.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring drug therapy, including cell based therapies. The methods of the invention can also be used in prognosis of a disease or disease condition. Examples of such disease or disease conditions include inflammation (e.g., inflammation caused by arthritis, for example, rheumatoid arthritis), cancer (e.g., colorectal, ovarian, lung, breast, prostate, cervical, skin, brain, gastrointestinal, mouth, esophageal, bone), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections, including Acquired Immunodeficiency Syndrome), immunologic disease (e.g., an autoimmune disorder, lymphoma, multiple sclerosis, rheumatoid arthritis, diabetes mellitus), central nervous system disease (e.g., a neurodegenerative disease, such as Parkinson's disease or Alzheimer's disease), inherited diseases, metabolic diseases, environmental diseases (e.g., lead, mercury and radioactive poisoning, skin cancer), and bone-related disease (e.g., osteoporosis, primary and metastatic bone tumors, osteoarthritis). The methods of the invention can therefore be used, for example, to determine the presence of tumor cells and localization of tumor cells, the presence and localization of inflammation, including the presence of activated macrophages, for instance in atherosclerosis or arthritis, the presence and localization of vascular disease including areas at risk for acute occlusion (i.e., vulnerable plaques) in coronary and peripheral arteries, regions of expanding aneurysms, unstable plaque in carotid arteries, and ischemic areas. The methods and compounds (compositions) of the invention can also be used in identification and evaluation of apoptosis, necrosis, hypoxia and angiogenesis.

Optical imaging modalities and measurement techniques include, but are not limited to, fluorescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography, and measurement of light scattering, absorption, polarisation, luminescence, fluorescence lifetime, quantum yield, and quenching.

The compounds (compositions) and methods of the present invention can be used in combination with other imaging compositions and methods. For example, the methods of the present invention can be used in combination with other traditional imaging modalities such as X-ray, computed tomography (CT), positron emission tomography (PET), single photon computerized tomography (SPECT), and magnetic resonance imaging (MRI). For instance, the compounds (compositions) and methods of the present invention can be used in combination with CT and MR imaging to obtain both anatomical and biological information simultaneously, for example, by co-registration of a tomographic image with an image generated by another imaging modality. In particular, the combination with MRI or CT is preferable, given the high spatial resolution of these imaging techniques. The compounds (compositions) and methods of the present invention can also be used in combination with X-ray, CT, PET, SPECT and MR contrast agents or the fluorescent silicon nanoparticle imaging probes of the present invention may also contain components, such as iodine, gadolinium atoms and radioactive isotopes, which can be detected using CT, PET, SPECT, and MR imaging modalities in combination with optical imaging.

Kits

The compounds (compositions) described herein can be packaged as a kit, which may optionally include instructions for using the fluorochromes or biocompatible fluorescent molecules in various exemplary applications. Non-limiting examples include kits that contain, e.g., the compounds (compositions) in a powder or lyophilized form, and instructions for using, including reconstituting, dosage information, and storage information for in vivo and/or in vitro applications. Kits may optionally contain containers of the compounds (compositions) in a liquid form ready for use, or requiring further mixing with solutions for administration. For in vivo applications, the kit may contain the compounds (compositions) in a dosage and form suitable for a particular application, e.g. a liquid in a vial, a topical creams, etc.

The kit can include optional components that aid in the administration of the unit dose to subjects, such as vials for reconstituting powder forms, syringes for injection, customized IV delivery systems, inhalers, etc. The kits may be supplied in either a container which is provided with a seal which is suitable for single or multiple puncturing with a hypodermic needle (e.g. a crimped-on septum seal closure) while maintaining sterile integrity. Such containers may contain single or multiple subject doses. Additionally, the unit dose kit can contain customized components that aid in the detection of the compounds (compositions) in vivo or in vitro, e.g., specialized endoscopes, light filters. The kits may also contain instructions for preparation and administration of the compounds (compositions). The kit may be manufactured as a single use unit dose for one subject, multiple uses for a particular subject; or the kit may contain multiple doses suitable for administration to multiple subjects ("bulk packaging"). The kit components may be assembled in cartons, blister packs, bottles, tubes, and the like.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

EXAMPLES

The following non limiting examples demonstrate the synthesis of nicotinic acid and picolinic acid derived near infrared fluorophores. Representative materials and methods that may be used in preparing the compounds of the invention are described further below. All chemicals and solvents (reagent grade) were used as supplied from the vendors cited without further purification.

The analytical and preparative HPLC methods generally utilized are:

| | | |
|---|---|---|
| A | Column: | Agilent Zorbax 80 Å, Extend C18, 4.6 × 250 mm (5 µm). |
| | Mobile Phase: | Acetonitrile and 25 mM triethylammonium acetate. |
| B | Column: | Varian Dynamax, 100 Å, C18, 41.4 × 250 mm. |
| | Mobile Phase: | Acetonitrile and 25 mM triethylammonium acetate. |
| C | Column: | Phenomenex Jupiter, 300 Å, C18 |
| | Mobile Phase: | Acetonitrile and 25 mM triethylammonium acetate. |

Example 1

Synthesis of Example 1

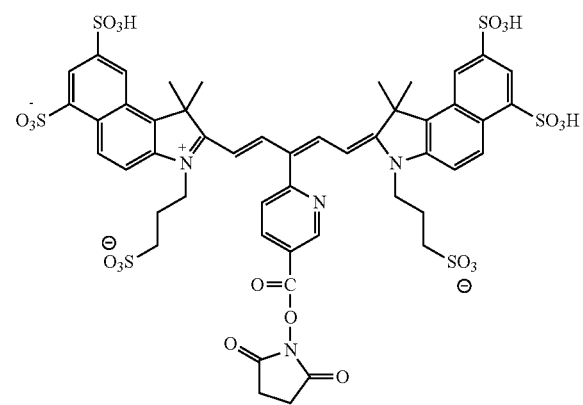

Part A. 6-hydrazino-1,3-naphthalene disulfonate (I)

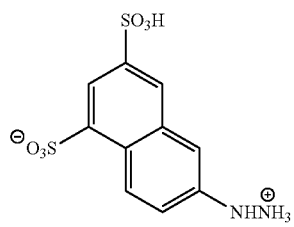

6-Amino-1,3-naphthalene disulfonate disodium salt (10 g, 29 mmol) (TCI) was dissolved in 30 mL of water and added to 50 mL of water and 15 mL of concentrated hydrochloric acid. The slurry was cooled to <0° C. in an ice/acetone bath and sodium nitrite (2.2 g, 32 mmol, Aldrich) was added in 40 mL of cold water drop-wise over 10 minutes. Stannous chloride (11 g, 58 mmol) (Aldrich) was dissolved in 30 mL water and 6 mL concentrated hydrochloric acid, cooled to 0° C. and added to the reaction mixture over 10 minutes. The resulting solution was stirred and allowed to warm to room temperature over 3 hours resulting in a clear, brown solution. The solution was reduced in volume by rotary evaporation and the product precipitated by the addition of isopropanol. Product (I) was filtered, washed with isopropanol and dried in vacuum.

Part B. 2,3,3-trimethylbenzindole-5,7-disulfonate (II)

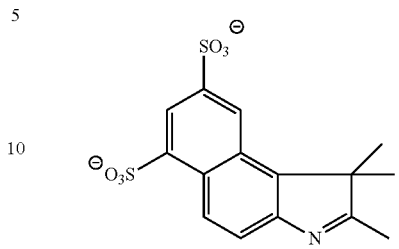

6-Hydrazino-1,3-naphthalene disulfonated (10 g, 25 mmol), isopropyl methyl ketone (12 g, 140 mmol, Aldrich) and potassium acetate (6 g, 61 mmol) were combined in 75 mL glacial acetic acid and heated to 145° C. for 22 hours. The solution was cooled and the acetic acid was removed by rotary evaporation. The residue was dissolved in methanol and filtered. The product (II) was then precipitated from the methanol filtrate with isopropanol and filtered, washed with isopropanol and ether and dried in vacuum.

Part C. 2,3,3-trimethyl-1-(3-sulfonatopropyl)benzindolinium-5,7-disulfonate (III)

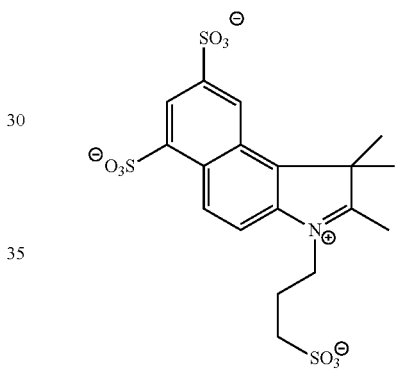

2,3,3-Trimethylbenzindole-6,8-disulfonate (2.2 g, 5 mmol) was dissolved in 50 mL of dry DMF resulting in a clear orange solution. 1,3-propanesultone (2.8 g, 23 mmol, Aldrich) was added and the solution was heated to 145° C. in a sealed tube for 15 hours, turning dark purple in color. The solution was cooled and poured into 150 mL 2-propanol. The mixture was centrifuged and the solvent decanted off. The solid product was washed on a filter with three 50 mL portions of 2-propanol followed by 50 mL of ether and dried in vacuum, resulting in 2.5 g of a dark purple solid (90%). MALDI-TOF-MS m/e 492.05 [M]+ calculated for $C_{18}H_{22}NO_9S_3$, found 492.05.

Part D: Preparation of Compound IV

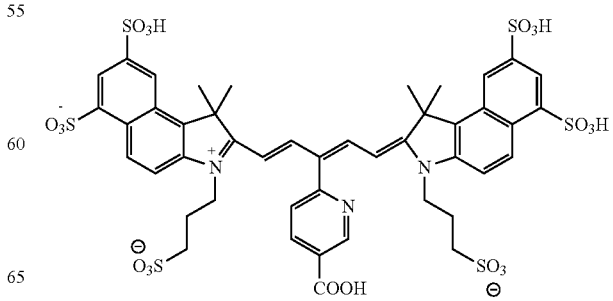

A 100 mL round bottom flask, fitted with a reflux condenser was charged with 2,3,3-trimethyl-1-(3-sulfonatopropyl)benzindolinium-5,7-disulfonate (565 mg, 1 mmol), 2-(3-hydroxycarbonyl-6-pyridyl)-malondialdehyde (98 mg, 0.5 mmol), and sodium acetate (585 mg, 7.1 mmol). Acetic anhydride (10 mL) and acetic acid (10 mL) were added to the flask, and the mixture was heated to reflux for 8 h, cooled down to room temp and 25 mL of ethyl acetate was added. The dark blue dye precipitate was collected by filtration, which was dissolved in 20 mL of water and purified by preparative reversed phase HPLC to afford the compound IV as powder. Yield, 285 mg, 50%. MALDI MS: Expected, 1139.09; Found, 1139.6732

Part E: Preparation of Example 1

Compound IV (11.4 mg, 0.01 mmol) was mixed with disuccinimidyl dicarbonate (DSC, 5 mg, 0.02 mmol)) and N,N-dimethylaminopyridine (DMAP, 2 mg, 0.016 mmol)) in 500 μL of dry DMF, and heated to 70° C. After 30 min cold ethyl acetate (500 μL) was added to the reaction mixture to precipitate the product out, which was filtered, dried under vacuum and stored at 4° C.

Example 2

Synthesis of Example 2

Part A: Preparation of Compound V

Compound V was prepared from potassium, 2,3,3-trimethyl-1-ethyl-benzindolinium-5,7-disulfonate (184 mg, 0.423 mmol), 2-(3-hydroxycarbonyl-6-pyridyl)-malondialdehyde (40 mg, 0.21 mmol), and sodium acetate (300 mg, 3.66 mmol) mixed in 6 mL of acetic anhydride and 6 mL of acetic acid. After heating at 125° C. for 16 hours, the product was precipitated from ethyl acetate and purified by reversed phase HPLC. The product in a powder form was obtained after speed vacuum drying of the HPLC fi-actions. MALDI. m/z calculated (found) for M$^+$: 952.05 (952.16). Yield, 140 mg, 70%.

Part B: Preparation of Example 2

One equivalent of Compound V was mixed with two equivalents of disuccinimidyl dicarbonate (DSC) and one equivalent of N,N-dimethylaminopyridine (DMAP) in 0.5 mL of DMF, and heated to 70° C. The reaction was complete within 30 min; the desired product was precipitated from the DMF solution by the addition of ethyl acetate, filtered, dried under vacuum and stored at 4° C.

Example 3

Synthesis of Example 3

Part A: Preparation of Compound VI

Compound VI was prepared from 2,3,3-Trimethyl-1-(3-sulfonatopropyl)-3H-benzindolinium-5,7-disulfonate (101 mg, 0.18 mmol), 2-(2-hydroxycarbonyl-6-pyridyl)-malonaldialdehyde (17.4 mg, 0.09 mmol), and sodium acetate (88 mg, 1.07 mmol) mixed in 6 mL of acetic anhydride and 6 mL of acetic acid. After heating at 125° C. for 4 hours, the product was precipitated from ethyl acetate and purified by reversed phase HPLC. The product was obtained in a powder form after speed vacuum drying of the HPLC fractions. MALDI. m/z calculated (found) for (M+1)$^+$: 1140.33 (1140.13). Yield, 67 mg, 65%.

Part B: Preparation of Example 3

One equivalent of compound VI was mixed with two equivalents of disuccinimidyl dicarbonate (DSC) and one equivalent of N,N-dimethylaminopyridine (DMAP) in 0.5 mL of DMF, and heated to 70° C. The progress of the reaction was monitored by HPLC. The reaction was complete within 30 min, following which the desired product was precipitated from the DMF solution by the addition of ethyl acetate, filtered, dried under vacuum and stored at 4° C.

Example 4

Synthesis of Example 4

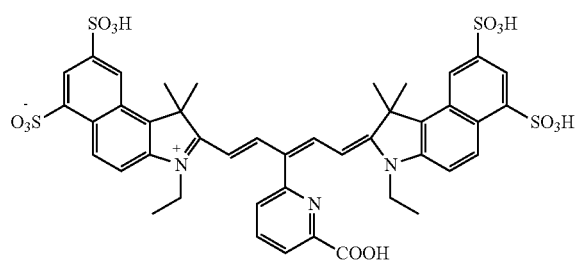

Example 4 is prepared from 2,3,3-Trimethyl-1-(ethyl)-3H-benzindolinium-5,7-disulfonate (0.18 mmol), 2-(2-hydroxycarbonyl-6-pyridyl)-malonaldialdehyde (0.09 mmol), and sodium acetate (88 mg, 1.07 mmol) mixed in 6 mL of acetic anhydride and 6 mL of acetic acid. After heating at 125° C. for 4 hours, the product is precipitated from ethyl acetate, purified by reversed phase HPLC and obtained in a powder form after speed vacuum drying of the HPLC fractions.

Example 5

Synthesis of Example 5

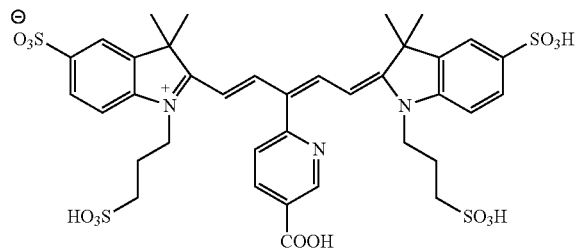

2,3,3-Trimethyl-1-(3-sulfonatopropyl)-indolinium-5-sulfonate (115 mg, 0.28 mmol), 2-(3-hydroxycarbonyl-6-pyridyl)-malonaldialdehyde (27 mg, 0.14 mmol), and sodium acetate (80 mg, 1.0 mmol) were mixed in 5 mL of acetic anhydride and 5 mL of acetic acid. After heating at 125° C. for 2 hours, reaction mixture was cooled down and the product was precipitated from ethyl acetate, followed by purification by reversed phase HPLC. The product was obtained in a powder form after speed vacuum drying of the HPLC fractions. Yield, 87 mg, 70%. Abs. max (water): 635 nm; Em. Max (water): 653 nm.

Example 6

Synthesis of Example 6

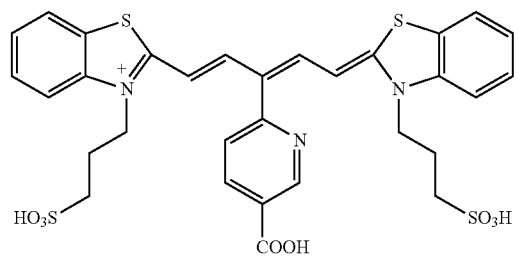

2-Methyl-1 (3-sulfonatopropyl)-benzothiazolium inner salt (150 mg, 0.55 mmol) and 2-(3-hydroxycarbonyl-6-pyridyl)-malonaldialdehyde (52 mg, 0.27 mmol) were added to a mixture of 2-methoxy ethanol and toluene (2:1, v/v) and heated to reflux at 150° C. attached to a Dean-Stark condenser. After 4 hours, heating was stopped, cooled down and solvents were removed by rotary evaporation. The concentrated blue dye was purified using preparative HPLC. The product was obtained in a powder form after drying of the HPLC fractions on speed vacuum. Yield, 95 mg, 50%. Abs. max (water): 643 in; Em. Max (water): 663 nm.

Example 7

Synthesis of Example 7

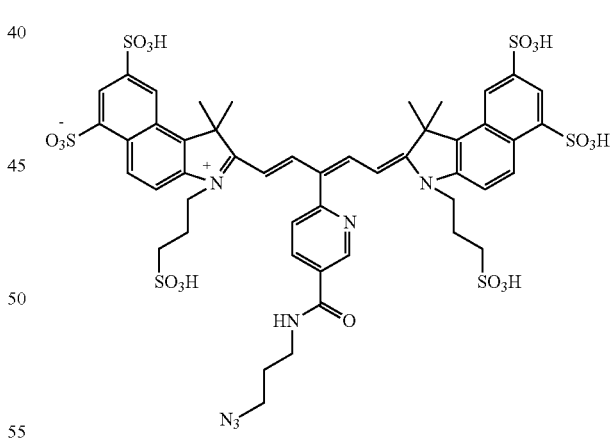

10 mg of the NHSE of Compound IV was dissolved in 100 uL dry DMF, to which was added a solution of 3-azidopropylamine (5 mg) in 20 uL dry DMSO, and the mixture was rotated at room temperature for one hour. 1 mL ether was added to the reaction mixture, and centrifuged for 10 minutes. The supernatant solution was discarded, and the residue was dried on speed vac for 5 minutes, redissolved in water and purified on a RPC18 semi-prep column. The fraction corresponding to the product (Example 7) was collected, and dried on speedvac which yielded 7.2 mg (60%). It was characterized by MALDI. Calculated: 1222.34. Found: 1222.54

Example 8

Synthesis of Example 8

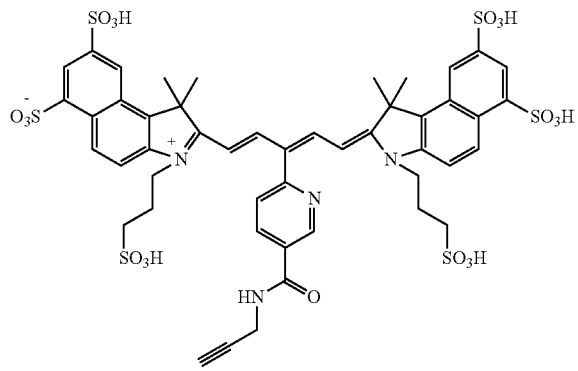

10 mg of the NHSE of Compound IV was dissolved in 100 uL dry DMF, to which was added a solution of 3-propargylamine (5 mg) in 10 uL dry DMSO, and the mixture was rotated at room temperature for one hour. 1 mL ether was added to the reaction mixture, and centrifuged for 10 minutes. The supernatant solution was discarded, and the residue was dried on speed vac for 5 minutes, redissolved in water and purified on a RPC18 semi-prep column. The fraction corresponding to the product (Example 8) was collected, and dried on speedvac. Yield: 6 mg (52%). It was characterized by MALDI. Calculated: 1177.32. Found: 1177.21

Example 9

Synthesis of Example 9

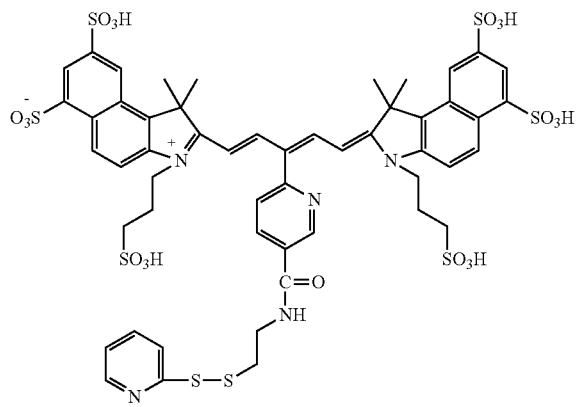

17 mg of the NHSE of Compound IV was dissolved in 250 uL dry DMF, to which was added a solution of 2-(2-aminoethyl-dithio)pyridine hydrochloride (11 mg) in 10 uL dry DMSO and 4 uL of triethylamine, and the mixture was rotated at room temperature for an overnight. 1 mL ethyl acetate was added to the reaction mixture, and centrifuged for 10 minutes. The supernatant solution was discarded, and the residue was dried on speed vac for 5 minutes, redissolved in water and purified on a RPC18 semi-prep column. The fraction corresponding to the product (Example 9) was collected, and dried on speedvac. Yield: 10 mg (65%). It was characterized by MALDI. Calculated: 1308.52. Found: 1308.54

Example 10

Cell Labeling

Mouse splenocytes were prepared as a single cell suspension, and the T cell subpopulation within the splenocyte preparation were enriched by passage over a column that removes B cells and macrophages (R & D kit, Mouse T-cell enrichment columns, MTCC500). T cells were centrifuged to generate a cell pellet of $10^7$ cells.

The supernatant was removed from the cell pellet, and a solution of 10 mg/ml of compound of Example 1 in 100 uL was added. Cells were incubated at room temperature for 5 minutes, followed by 2 rounds of centrifugation and resuspension in physiologic buffer to wash away unbound Example 1. Cells were assessed by fluorescence microscopy.

Example 11

Cell Labeling and In Vivo Imaging

Mouse 4T1 breast adenocarcinoma cells were centrifuged to generate a cell pellet of $10^7$ cells. The supernatant was removed from the cell pellet, and a solution of 10 mg/ml Example 1 in 100 uL was added. Cells were incubated at room temperature for 5 minutes, followed by 2 rounds of centrifugation and resuspension in physiologic buffer to wash away unbound Example 1. Cells were assessed by fluorescence microscopy. Cells were injected intravenously into mice at $5 \times 10^5$ cells per mouse, and live mice were imaged by fluorescent molecular tomography immediately after injection and 24 hours after injection. As 4T1 cells primarily metastasize to the lungs, lung fluorescence is quantified.

Example 12

A solution of Example 1 was chemically linked to an amine presenting surface of nanoparticles to yield a biocompatible fluorescent molecule for in vivo optical imaging. The tumor cell line HT-29 (human colon carcinoma/HTB-38) was obtained from ATCC (Manassas, Va.). HT-29 cells were grown in McCoy's supplemented with 10% FBS at 37° C. in a humidified atmosphere containing 5% $CO_2$. Exponentially growing cells were trypsinized and re-suspended in Hank's Balanced Salt Solution at a concentration of $3 \times 10^7$ cells/ml. Female NU/NU mice 6-8 weeks old (Charles River Laboratory, Wilmington, Mass.) were injected subcutaneously with $3 \times 10^6$ HT-29 cells bilaterally in the first mammary fat pads. One week later, when tumors were approximately 30 $mm^3$, mice were injected intravenously with the fluorescent molecule, (in 150 μl of 1×PBS) and imaged after 24 hrs on a fluorescence reflectance system (FRI, Kodak 2000 MM) system. Results are shown in FIG. 1

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of the formula (2):

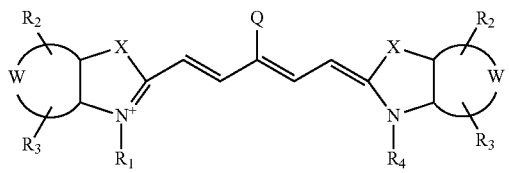

or a salt thereof, wherein:
- X is independently selected from the group consisting of $C(CH_2Y_1)(CH_2Y_2)$, O, S, and Se;
- $Y_1$ and $Y_2$ are independently selected from the group consisting of H, $C_1$-$C_{20}$ aliphatic group, and a $C_1$-$C_{20}$ aliphatic group wherein one or more methylene groups are replaced by O, S, or NH;
- W represents a benzo-condensed ring or a naphtho-condensed ring;
- $R_1$ is selected from the group consisting of H, $(CH_2)_xCH_3$, $(CH_2)_nSO^-$ and $(CH_2)_nSO_3H$, wherein x is an integer selected from 0 to 6 and n is an integer selected from 2 to 6;
- $R_4$ is selected from the group consisting of H, $(CH_2)_xCH_3$, $(CH_2)_nSO_3^-$ and $(CH_2)_nSO_3H$, wherein x is an integer selected from 0 to 6 and n is an integer selected from 2 to 6;
- $R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;
- Q is a heteroaryl ring substituted with —$CO_2H$, —C(O)-halide, —C(O)O- benzotriazolyl, —C(O)O—N-succinimidyl, —C(O)O-tetrafluorophenyl, —C(O)O-pentafluorophenyl, —C(O)O-imidazolyl, or —C(O)O-p-nitrophenyl; or
- Q is selected from the group consisting of

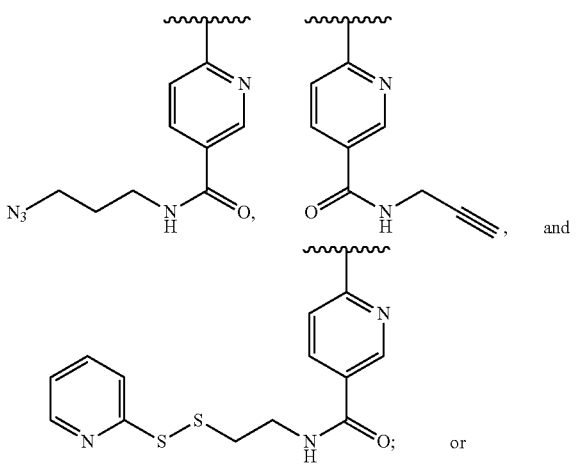

Q is a 6-membered heteroaryl ring substituted with —C(=O)R, wherein R is a saturated straight-chain hydrocarbon, a branched hydrocarbon, or a cyclic hydrocarbon.

2. The compound of claim 1, wherein Q is selected from the group consisting of carboxyl substituted pyridine, pyrimidone, pyrazine, and pyridazine.

3. The compound of claim 2, wherein Q is carboxyl substituted pyridine.

4. The compound of claim 3, wherein Q is selected from the group consisting of isonicotinic acid, nicotinic acid and picolinic acid.

5. The compound of claim 4, wherein Q is represented by a structural formula selected from the group consisting of:

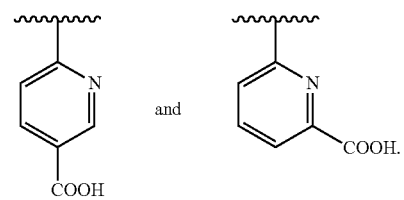

6. The compound of claim 1, wherein at least one of the moieties $R_1$ to $R_3$ is, or contains a sulphonic acid moiety or a sulphonate moiety.

7. The compound of claim 1, wherein $R_1$ and $R_4$ are independently —H, $(CH_2)_nSO_3^-$ or $(CH_2)_nSO_3H$.

8. The compound of claim 1, having any of the formulae:

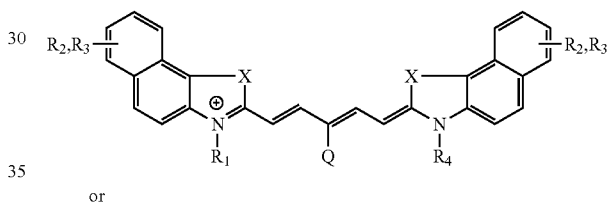

or

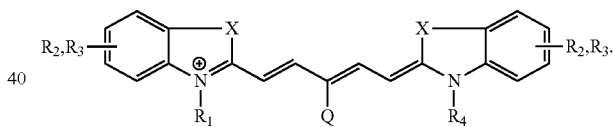

9. The compound of claim 1, having any of the formulae:

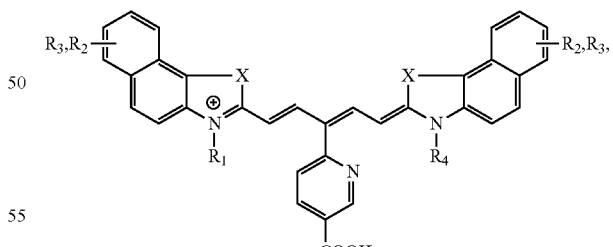

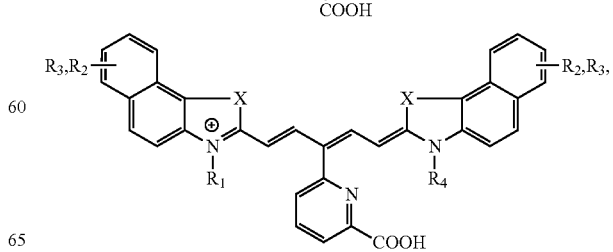

-continued

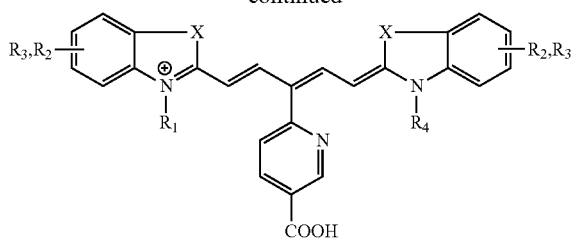

or

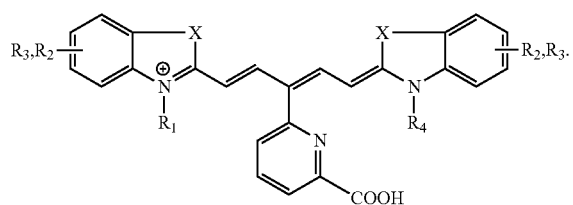

10. A compound of the formula (2):

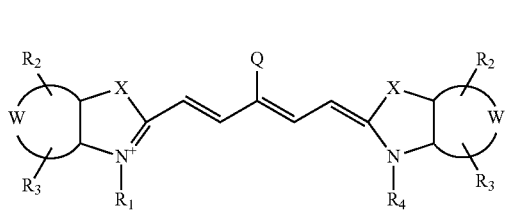

or a salt thereof, wherein:
- X is independently selected from the group consisting of $C(CH_2Y_1)(CH_2Y_2)$, O, S, and Se;
- $Y_1$ and $Y_2$ are independently selected from the group consisting of H, $C_1$-$C_{20}$ aliphatic group, and a $C_1$-$C_{20}$ aliphatic group wherein one or more methylene groups are replaced by O, S, or NH;
- W represents a benzo-condensed ring or a naphtho-condensed ring;
- $R_1$ is selected from the group consisting of $(CH_2)_xCH_3$, $(CH_2)_nSO_3^{31}$ and $(CH_2)_nSO_3H$, wherein x is an integer selected from 0 to 6 and n is an integer selected from 2 to 6;
- $R_4$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;
- $R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;
- Q is a heteroaryl ring substituted with —$CO_2H$, —C(O)-halide, —C(O)O-benzotriazolyl, —C(O)O—N-succinimidyl, —C(O)O-tetrafluorophenyl, —C(O)O-pentafluorophenyl, —C(O)O-imidazolyl, or —C(O)O-p-nitrophenyl; or Q is selected from the group consisting of

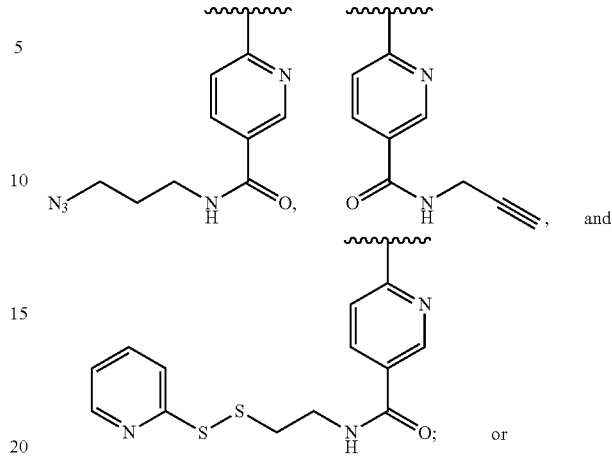

Q is a 6-membered heteroaryl ring substituted with —C(=O)R, wherein R is a saturated straight-chain hydrocarbon, a branched hydrocarbon, or a cyclic hydrocarbon.

11. The compound of claim 10, wherein Q is selected from the group consisting of carboxyl substituted pyridine, pyrimidone, pyrazine, and pyridazine.

12. The compound of claim 11, wherein Q is carboxyl substituted pyridine.

13. The compound of claim 12, wherein Q is selected from the group consisting of isonicotinic acid, nicotinic acid and picolinic acid.

14. The compound of claim 13, wherein Q is represented by a structural formula selected from the group consisting of:

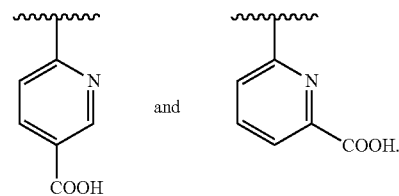

15. The compound of claim 10, wherein at least one of the moieties $R_1$ to $R_3$ is, or contains a sulphonic acid moiety or a sulphonate moiety.

16. The compound of claim 10, wherein $R_1$ and $R_4$ are independently $(CH_2)_nSO_3^-$ or $(CH_2)_nSO_3H$.

17. The compound of claim 10 having any of the formulae:

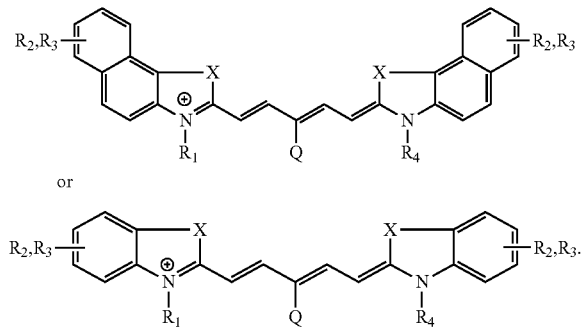

18. The compound of claim 10 having any of the formulae:
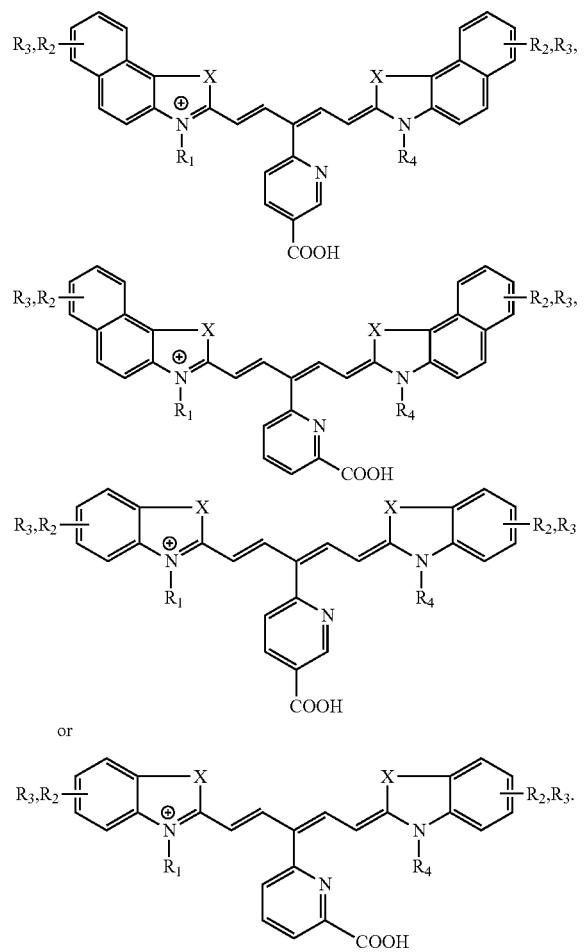
or
19. The compound of claim 1, wherein Q is represented by a structural formula selected from the group consisting of:
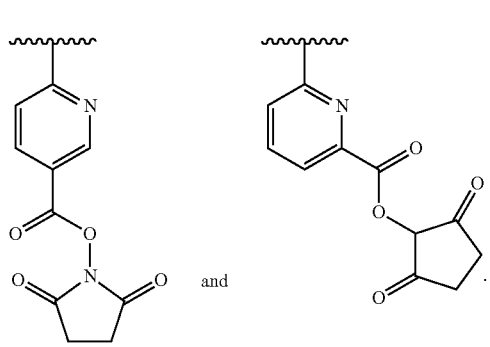
20. The compound of claim 10, wherein Q is represented by a structural formula selected from the group consisting of:
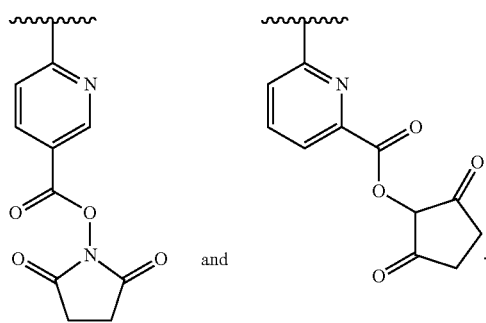
* * * * *

UNITED STATES PATENT AND TRADEMARK OFFICE
CERTIFICATE OF CORRECTION

PATENT NO. : 8,173,819 B2
APPLICATION NO. : 12/065391
DATED : May 8, 2012
INVENTOR(S) : Milind Rajopadhye et al.

Page 1 of 1

It is certified that error appears in the above-identified patent and that said Letters Patent is hereby corrected as shown below:

Claim number 10, column 37, line 50, replace "$(CH_2)_nSO_3^{31}$" with --$(CH_2)_nSO_3^-$.--

Claim number 19, column 40, lines 5-16, replace 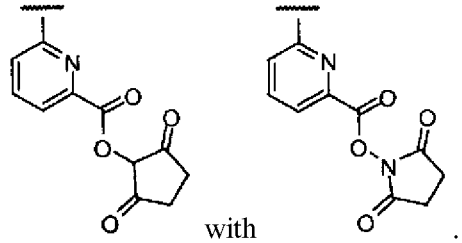 .

Claim number 20, column 40, lines 25-36, replace 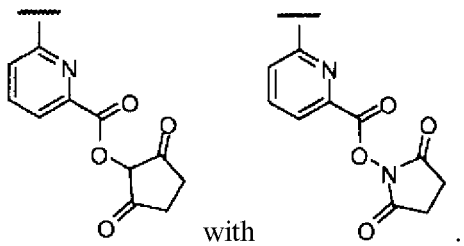 .

Signed and Sealed this
Tenth Day of July, 2012

David J. Kappos
*Director of the United States Patent and Trademark Office*